United States Patent
Gerecht et al.

(10) Patent No.: US 9,428,735 B2
(45) Date of Patent: *Aug. 30, 2016

(54) SMOOTH MUSCLE-LIKE CELLS (SMLCS) DERVIDED FROM HUMAN PLURIPOTENT STEM CELLS

(75) Inventors: Sharon Gerecht, Baltimore, MD (US); Donny Hanjaya-Putra, Baltimore, MD (US); Elaine Tuong Vo, Baltimore, MD (US); Maureen Wanjare, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/581,341

(22) PCT Filed: Feb. 25, 2011

(86) PCT No.: PCT/US2011/026294
§ 371 (c)(1),
(2), (4) Date: Aug. 27, 2012

(87) PCT Pub. No.: WO2011/106681
PCT Pub. Date: Sep. 1, 2011

(65) Prior Publication Data
US 2012/0322151 A1   Dec. 20, 2012

Related U.S. Application Data

(60) Provisional application No. 61/308,014, filed on Feb. 25, 2010.

(51) Int. Cl.
*C12N 5/071* (2010.01)

(52) U.S. Cl.
CPC ......... *C12N 5/0691* (2013.01); *C12N 2500/44* (2013.01); *C12N 2501/135* (2013.01); *C12N 2501/15* (2013.01); *C12N 2506/02* (2013.01); *C12N 2533/54* (2013.01)

(58) Field of Classification Search
CPC .......... C12N 5/0607; C12N 2501/135; C12N 2506/03; C12N 2506/02; C12N 2501/15
USPC .......................................... 435/366, 325, 377
See application file for complete search history.

(56) References Cited

U.S. PATENT DOCUMENTS

| | | |
|---|---|---|
| 2005/0112106 A1 | 5/2005 | Gerecht-Nir et al. |
| 2009/0123430 A1 | 5/2009 | De Sousa |
| 2010/0216181 A1 | 8/2010 | Daigh et al. |
| 2010/0279403 A1 | 11/2010 | Rajesh et al. |
| 2011/0305672 A1 | 12/2011 | Dalton et al. |
| 2012/0015395 A1 | 1/2012 | Shusta et al. |
| 2012/0295347 A1 | 11/2012 | Kessler |

FOREIGN PATENT DOCUMENTS

| | | |
|---|---|---|
| EP | 2277993 A1 | 1/2011 |
| WO | WO-03-010303 A1 | 2/2003 |
| WO | WO-2010/099539 A1 | 9/2010 |
| WO | WO-2011-090684 A2 | 7/2011 |
| WO | WO-2011/106681 A2 | 9/2011 |
| WO | WO-2012/006440 A2 | 1/2012 |
| WO | WO-2012/168167 A1 | 12/2012 |

OTHER PUBLICATIONS

Yu et al., Oxidized low density lipoprotein-induced transdifferentiation of bone marrow-derived smooth muscle like cells into foam-like cells in vitro. International Journal of Experimental Pathology, vol. 91 (online Dec. 22, 2009) pp. 24-33.*
Kurpinski et al., Transforming growth factor-B and ntoch signaling mediate stem cell differentiation into smooth muscle cells. Stem Cells, vol. 28 (online Feb. 9, 2010) pp. 734-742.*
Kobayashi et al., Mechanical stress promotes the expression of smooth muscle-like properties in marrow stromal cells. Experimental Hematology, vol. 32 (2004) pp. 1238-1245.*
van Kooten et al., Fluid shear induced endothelial cell detachment from modified polystyrene substrata. Colloids and Surfaces B: Biointerfaces, vol. 3 No. 3 (Nov. 25, 1994) pp. 147-158.*
Freshney, R. Ian (Culture of Animal Cells: A Manual of Basic Techniques and Specialized Applications, 6th ed. Wiley Blackwell, 2011. pp. 163-186.*
Yu et al., "Oxidized low density lipoprotein-induced transdifferentiation of bone marrow-derived smooth muscle-like cells into foam-like cells in vitro" International Journal of Experimental Pathology, vol. 91, pp. 24-33 (Dec. 22, 2009).
Doi et al., "Notch signaling regulates the differentiation of bone marrow-derived cells into smooth muscle-like cells during arterial lesion formation" Biochemical and Biophysical Communications, vol. 381, pp. 654-659 (Feb. 27, 2009).
Sugiyama et al., "Characterization of smooth muscle-like cells in circulating human peripheral Blood", Atherosclerosis, 2006, vol. 187, pp. 351-362.

(Continued)

*Primary Examiner* — Kara Johnson
(74) *Attorney, Agent, or Firm* — Venable LLP; Keith G. Haddaway; Miguel A. Lopez

(57) ABSTRACT

This invention relates, e.g., to a method for differentiating mammalian (e.g., human) pluripotent stem cells (PSCs) into smooth muscle-like cells (SMLCs) in vitro, comprising a) plating a single-cell suspension of PSCs that are smaller than 50 μm at a seeding concentration of about $5 \times 10^4$ cells/cm²-about $1 \times 10^5$ cells/cm² onto a suitable surface, and culturing the cells under conditions which prevent the PSCs from aggregating and induce differentiation of the PSCs into vasculogenic progenitor cells; b) harvesting the cultured cells of step a) and separating them into a single cell suspension of cells that are smaller than 50 μm; and c) plating the single cell suspension of step b) at a seeding concentration of about $1 \times 10^4$ cells/cm²-about $5 \times 10^4$ cells/cm² on a suitable surface, and culturing the cells in a differentiation medium that is supplemented with platelet-derived growth factor BB (PDGF-BB) and transforming growth factor-beta 1 (TGF β1), for a sufficient period of time to allow the vasculogenic progenitor cells to mature into SMLCs. In one embodiment of the invention, the cells from step c) are further subjected to a shear force of at least 1 dyne/cm² for a time period sufficient to enhance differentiation, maturation and/or functionality of the cells.

25 Claims, 11 Drawing Sheets

(56) References Cited

OTHER PUBLICATIONS

Sone et al. "Pathway for Differentiation of Human Embryonic Stem Cells to Vascular Cell Components and Their Potential for Vascular Regeneration", Arterioscler Thromb. Vasco Biol., 2007, vol. 27, pp. 2127-2134.
Pertoft, H. "Fractionation of cells and subcellular particles with Percoll", J. Bioochem Biophys Methods, 2000; vol. 44, pp. 1-30.
B. E. Reubinoff et. Al. "Embryonic stem cell lines from human blastocysts: somatic differentiation in vitro," Nature Biotechnology, 2000, vol. 18, No. 4, pp. 399-404.
Shuldiner, M et al. "Effects of eight growth factors on the differentiation of cells derived from human embryonic stem cells", 2000, PNAS USA, vol. 97, pp. 11307-11312.
Gerecht-Nir et al. "Human Embryonic Stem Cells as an In Vitro Model for Human Vascular Development and the Induction of Vascular Differentiation", Laboratory Investigation, 2003, vol. 83, pp. 1811-1820.
Hanjaya-Putra et al. "Vascular endothelial growth factor and substrate mechanics regulate in vitro tubulogenesis of endothelial progenitor cells", J Cell Mol Med, 2009, vol. 14, No. 10, pp. 2436-2447.
Gong et al. "Small-diameter human vessel wall engineered from bone marrow-derived mesenchymal stem cells (hMSCs)", FASEB Journal, 2008, vol. 22, pp. 1635-1648.
Duband et al. "Calponin and SM 22 as differentiation markers of smooth muscle: spatiotemporal distribution during avian embryonic development", Differentiation, 1993, vol. 55, pp. 1-11.
Kuro-o et al. "Developmentally regulated expression of vascular smooth muscle myosin heavy chain isoforms", Journal of Biological Chemistry, 1989, vol. 264, pp. 18272-18275.
Aikawa et al. (1993) Circ Res 107,1000-1012.
Bettinger et al. "Enhancement of In Vitro Capillary Tube Formation by Substrate Nanotopography", Adv. Mater, 2008, vol. 20, pp. 99-103.
Carmeliet P. "Mechanisms of Angiogenesis and Arteriogenesis", Nat. Med, 2000, vol. 6, pp. 389-395.
Hirschi KK et al. Smooth Muscle Stem Cells:, Anatomical Record-Par A Discoveries in Molecular, Cellular, and Evolutionary Biology, 2004, vol. 276, pp. 22-33.
Jain RK. "Molecular regulation of vessel maturation", Nature Medicine, 2003, vol. 9, pp. 685-693.
Hirschi KK et. al. "PDGF, TGF-β, and Heterotypic Cell-Cell Interactions Mediate Endothelial Cell-induced Recruitment of 10T1/2 Cells and Their Differentiation to a Smooth Muscle Fate", Journal of Cell Biology, 1998, vol. 141, pp. 805-814.
Folkman J et al. "Long-term culture of capillary endothelial cells", PNAS USA, 1979, vol. 76, pp. 5217-5221.
Darland DC et al. "TGFβ is required for the formation of capillary-like structures in three-dimensional cocultures of 10T1/2 and endothelial cells", Angiogenesis, 2001, vol. 4, pp. 11-20.
Melero-Martin JM et al. "Engineering robust and functional vascular networks in vivo with human adult and cord blood-derived progenitor cells", Circulation Research, 2008, vol. 103, pp. 194-202.
Au P et al. "Bone marrow derived mesenchymal stem cells facilitate engineering of long-lasting functional vasculature", Blood, 2008, vol. 111, pp. 4551-4558.
Traktuev DO et al. "A population of multipotent CD34-positive adipose stromal cells share pericyte and mesenchymal surface markers, reside in a perlendothelial location, and stabilize endothelial networks", Circulation Research, 2008, vol. 102, pp. 77-85.
Rodriguez et al. "Clonogenic multi potent stem cells in human adipose tissue differentiate into functional smooth muscle cells". PNAS USA, 2006, vol. 103, pp. 12167-12172.
Chen S et al. "Transforming growth factor-beta-induced differentiation of smooth muscle from a neural crest stem cell line", Circulation Research, 2004, vol. 94, pp. 1195-1202.

Taura D et al. "Induction and isolation of vascular cells from human induced pluripotent stem cells-brief report", Arterioscler Thromb Vasc Biol, 2009, vol. 29, pp. 1100-1103.
Lindskog et al. "New insights to vascular smooth muscle cell and pericyte differentiation of mouse embryonic stem cells in vitro" Arterioscler Thromb Vasc Biol, 2006, vol. 26, pp. 1457-1464.
Xie et al. "A comparison of murine smooth muscle cells generated from embryonic versus induced pluripotent stem cells" Stem Cells Dev, 2009, vol. 18, pp. 741-748.
Narazaki G et al. "Directed and systematic differentiation of cardiovascular cells from mouse induced pluripotent stem cells" Circulation, 2008, vol. 118, pp. 498-506.
Potta SP et al. "Functional characterization and transcriptome analysis of embryonic stem cell derived contractile smooth muscle cells" Hypertension, 2009, vol. 53, pp. 196-204.
Hirschi KK, et al. "Assessing Identity, phenotype, and fate of endothelial progenitor cells", Arteriosclerosis, Thrombosis, and Vascular Biology, 2008, vol. 28, pp. 1584-1595.
Mead LE et al. "Isolation and characterization of endothelial progenitor cells from human blood" *Current protocols in Stem Cell Biology* 2C.1.1-2C.1.27, (2008).
Prater DN, et al. "Working hypothesis to redefine endothelial progenitor cells" Leukemia, 2007, vol. 21, pp. 1141-1149.
Timmermans F et al. "Endothelial progenitor cells: Identity defined?" Journal of Cellular and Molecular Medicine, 2009, vol. 13, pp. 87-102.
Gong Z et al. "Influence of culture medium on smooth muscle cell differentiation from human bone marrow-derived mesenchymal stem cells" Tissue Engineering—Part A, 2009, vol. 15, pp. 319-330.
Sone et al. "Different differentiation kinetics of vascular progenitor cells in primate and mouse embryonic stem cells" Circulation, 2003, vol. 107, pp. 2085-2088.
Levenberg S, et al. Endothelial cells derived from human embryonic stem cells PNAS USA, 2002, vol. 99, pp. 4391-4396.
Kaufman et al. "Hematopoietic colony-forming cells derived from human embryonic stem cells" PNAS USA, 2001, vol. 98, pp. 10716-10721.
Au P et al. "Differential in vivo potential of endothelial progenitor cells from human umbilical cord blood and adult peripheral blood to form functional long-lasting vessels" Blood, 2007, vol. 111, pp. 1302-1305.
Shah NM et al. "Alternative neural crest cells fates are instructively promoted by TGD-Beta superfamily members" Cell, 1996, vol. 85, pp. 331-343.
James D et al. "Expansion and maintenance of human embryonic stem cell-derived endothelial cells by TGF (beta) inhibition is ldl dependent" Nat Biotech, 2010, vol. 28, pp. 161-166.
Solan A et al. "Age effects on Vascular Smooth muscle: An engineered tissue approach" Cell Transplantation, 2005, vol. 14, pp. 481-488.
Rensen SSM, et al. "Regulation and characteristics of vascular smooth muscle cell phenotypic diversity" Netherlands Heart Journal, 2007, vol. 15, pp. 100-108.
Carmeliet, P. "Angiogenesis in health and disease" Nature Medicine, 2003, vol. 9, pp. 653-660.
Tsai, M-C et al. "Shear Stress Induces Synthetic-to-Contractile Phenotypic Modulation in Smooth Muscle Cells via Peroxisome Proliferator-Activated Receptor (alpha)/(delta) Activations by Prostacyclin Released by Sheared Endothelial Cells" Circ Res, 2009, vol. 105, pp. 471-480.
Hirschi KK, et al. "Pericytes in the microvasculature" Cardiovascular Research, 1996, vol. 32, pp. 687-698.
Ding Ret al. "Endothelial-mesenchymal interactions in vitro reveal molecular mechanisms of smooth muscle/pericyte differentiation" Stem Cells and Development, 2004, vol. 13, pp. 509-520.
Koike et al. "Tissue engineering: creation of long-lasting blood vessels" Nature, 2004, vol. 428, pp. 138-139.
Vo et al. "Smooth-Muscle-Like Cells Derived from Human Embryonic Stem Cells Support and Augment Cord-Like Structures In Vitro." Stem Cell Rev and Rep vol. 6, No. 2 pp. 237-247, (2010).
Sinha et al. "Assessment of Contractility of Purified Smooth Muiscle Cells Derived from Embryonic Ste, Cells." *Stem Cells* 2006; 24: 1678-88.

(56) References Cited

OTHER PUBLICATIONS

Ingram et al. "Identification of a Novel Hierarchy of Endothelial Progenitor Cells Using Human Peripheral and Umbilical Cord Blood." *Blood* 2004; 104: 2752-60.
Gerecht-Nir et al. Human Embryonic Stem Cells as an in-vitro Model for Human Vascular Development and the Induction of Vascular Differentiation. Lab Invest. Dec. 2003; 83(12) [abstract only].
Wang et al. "Human Embryonic Stem Cells Maintained in the Absence of Mouse Embryonic Fibrolasts or Conditioned Media are Capable of Hematopietic Development." *Blood* 2005 105: 4598-4603.
Peerani et al. "Niche-mediated Control of Human Embryonic Stem Cell self-renewal and Differentiation." The EMBO Jounal (2007) 26, 4744-4755.
Stewart et al. "Deconstructing Human Embryonic Stem Cell Cultures: Niche Regulation of Self-Renewal and Pluripotency." J. Mol. Med. (2008) 86:875-86.
Xie et al: "A Highly Efficient Method to Differentiate Smooth Muscle Cells From Human Embryonic Stem Cells", Arteriosclerosis, Thrombosis, and Vascular Biology, vol. 27, No. 12, Dec. 1, 2007, pp. e311-e312 and data supplement.
Caspi et al. "Tissue Engineering of Vascularized Cardiac Muscle from Human Embryonic Stem Cells" Circ Res, 2007, vol. 100, pp. 263-272 and Data Supplement.
Ahmad et al., "Cross-correlation-based image acquisition technique for manually-scanned optical coherence tomography," Opt. Express 17(10), 8125-8136 (2009).
Becker et al., "State estimation and feedforward tremor suppression for a handheld micromanipulator with a Kalman filter," IEEE/RSJ, International Conference on Intelligent Robots and Systems, 5160-6165(2011).
Boppart et al., "Forward-imaging instruments for optical coherence tomography," Opt. Lett. 22(21), 1618-1620 (1997).
Boppart et al., "Optical coherence tomography: feasibility for basic research and image-guided surgery of breast cancer," Breast Cancer Res. Treatment 84(2), 85-97(2004).
Boppart et al., "Intraoperative assessment of microsurgery with three-dimensional optical coherence tomography," *Radiology*, vol. 208, pp. 81-86, 1998.
Chen et al., "Noninvasive imaging of in vivo blood flow velocity using optical Doppler tomography," Opt. Lett. 22(14), 1119-1121(1997).
Duncan et al., "Processing algorithms for tracking speckle shifts in optical elastography of biological tissues, " J. Biomed. Opt. 6(4), 418-426(2001).
Ha et al., "Compensation of motion artifacts in catheter-based optical frequency domain imaging," Opt. Express 18(11), 11418-11427 (2010).
Han et al., "Handheld forward-imaging needle endoscope for ophthalmic optical coherence tomography inspection," J. Biomed. Opt. 13(2), 020505(2008).
Huang et al., "Motion compensated fiber-optic confocal microscope based on a common-path optical coherence tomography distance sensor," Opt. Eng 50(8), 08320 (2011).
Huang et al., "Noncontact common-path Fourier domain optical coherence tomography method for in vitro intraocular lens power measurement", J. Biomed. Opt. 16(12), 126005(2011).
Huang et al., "Optical coherence tomography," Science, 254(5035), 1178-1181(1991).
Huang et al., "Real-time 3D and 4D Fourier domain Doppler optical coherence tomography based on dual graphics processing units," Biomed. Opt. Express 3(9), 2162-2174 ( 2012).
Huber et al., "Buffered Fourier domain mode locking: unidirectional swept laser sources for optical coherence tomography imaging at 370,000 lines/s," Opt. Lett., vol. 31, pp. 2975-2977, 2006.
Huo et al., "Forward-viewing resonant fiber-optic scanning endoscope of appropriate scanning speed for 3D OCT imaging," Opt. Express 18(14),14375-14384(2010).
Iftimia et al., "Adaptive ranging for optical coherence tomography," Opt. Express 12(17), 4025-4034 (2004).
Jafri et al., "Optical coherence tomography guided neurosurgical procedures in small rodents," J. Neurosci. Methods 176(2), 85-89 (2009).
Jung et al., "Three-dimensional optical coherence tomography employing a 2-axis microelectromechanical scanning mirror," IEEE J. Sel. Top. Quantum Electron. 11(4), 806-810(2005).
Kang et al., "Endoscopic functional Fourier domain common path optical coherence tomography for microsurgery," IEEE J. Sel. Top. Quantum Electron. 16(4), 781-792(2010).
Kang et al., "Real-time three-dimensional Fourier-domain optical coherence tomography video image guided microsurgeries," J. Biomed. Opt. 17(8), 081403 (2012).
Klein et al., "Megahertz OCT for ultrawide-field retinal imaging with a 1050nm Fourier domain mode-locked laser," Opt. Express, vol. 19, pp. 3044-3062, 2011.
Lee et al., "Motion correction for phase-resolved dynamic optical coherence tomography imaging of rodent cerebral cortex," Biomed. Opt. Express 19(22), 21258-21270 (2012).
Leitgeb et al., "Ultrahigh resolution Fourier domain optical coherence tomography," Opt. Express 12(10), 2156-2165(2004).
Liu et al., "Distortion-free freehand-scanning OCT implemented with real-time scanning speed variance correction," Opt. Express 20(15), 16567-16583 (2012).
Maguluri et al., "Three dimensional tracking for volumetric spectral-domain optical coherence tomography," Opt. Express 15(25), 16808-16817 ( 2007).
Potsaid et al., "Ultrahigh speed Spectral / Fourier domain OCT ophthalmic imaging at 70,000 to 312,500 axial scans per second," Opt. Express, vol. 16, pp. 15149-15169, 2008.
Singh et al., "Physiological tremor during retinal microsurgery," Proc. 28th Annual Conf. IEEE Eng. Med. Bio. Soc.,171-172(2002).
Song et al., "Active tremor cancellation by a "Smart" handheld vitreoretinal microsurgical tool using swept source optical coherence tomography," Opt. Express 20, 23414-23421 (2012).
Tan et al., "In-fiber common-path optical coherence tomography using a conical-tip fiber," Opt. Express 17(4),2375-2380(2009).
Vakhtin et al., "Common-path interferometer for frequency-domain optical coherence tomography," App. Opt. 42(34), 6935-6958 (2003).
Zhang et al., "Common-path low-coherence interferometry fiber-optic sensor guided microincision," J. Biomed. Opt. 16(9),095003(2011).
Zhang et al., "Real-time intraoperative 4D full-range FD-OCT based on the dual graphics processing units architecture for microsurgery guidance," Biomed. Opt. Express. 2(4), 764-770 (2011).
Zysk et al., "Optical coherence tomography: a review of clinical development from bench to bedside," J. Biomed. Opt. 12(5), 051403 (2007).
Hill et al., "Human Embryonic Stem Cell Derived Vascular Progenitor Cells Capable of Endothelial and Smooth Muscle Cell Function", Experimental Hematology, vol. 38, No. 3, pp. 246-257. (2010).
Vo et al., "Smooth-Muscle-Like Cells Derived From Human Embryonic Stem Cells Support and Augment Cord-Like Structures In Vitro", Stem Cells Reviews and Reports, vol. 6, No. 2, pp. 237-247. (2010).
Ball SG, Shuttleworth CA, Kielty CM. Platelet-derived growth factor receptors regulate mesenchymal stem cell fate: implications for neovascularization. Expert Opin Biol Ther 2010;10:57-71.
Beamish JA HP, Kottke-Marchant K, Marchant RE. Molecular regulation of contractile smooth muscle cell phenotype: implications for vascular tissue engineering. Tissue Eng Part B Rev. 2010;16:467-491.
Bertolino P, Deckers M, Lebrin F, ten Dijke P. Transforming Growth Factor-β Signal Transduction in Angiogenesis and Vascular Disorders. Chest 2005;128:585S-590S.
Cecchettini A, Rocchiccioli S, Boccardi C, Citti L. Chapter Two—Vascular Smooth-Muscle-Cell Activation: Proteomics Point of View. In: Kwang WJ, ed. International Review of Cell and Molecular Biology. vol. 288: Academic Press; 2011:43-99.

(56) References Cited

OTHER PUBLICATIONS

Chan-Park MB, Shen JY, Cao Y, Xiong Y, Liu Y, Rayatpisheh S et al. Biomimetic control of vascular smooth muscle cell morphology and phenotype for functional tissue-engineered small-diameter blood vessels. J Biomed Mater Res A 2009;88A:1104-1121.

Chen J, Kitchen CM, Streb JW, Miano JM. Myocardin: a component of a molecular switch for smooth muscle differentiation. J Mol Cell Cardiol. 2002;34:1345-1356.

Cheng L, Hansen NF, Zhao L, Du Y, Zou C, Donovan FX et al. Low incidence of DNA sequence variation in human induced pluripotent stem cells generated by nonintegrating plasmid expression. Cell Stem Cell 2012;10:337-344.

Chou BK, Mali P, Huang X, Ye Z, Dowey SN, Resar LM et al. Efficient human iPS cell derivation by a non-integrating plasmid from blood cells with unique epigenetic and gene expression signatures. Cell Res 2011;21:518-529.

Dempsey EC, Badesch DB, Dobyns EL, Stenmark KR. Enhanced growth capacity of neonatal pulmonary artery smooth muscle cells in vitro: Dependence on cell size, time from birth, insulin-like growth factor I, and auto-activation of protein Kinase C. J Cell Physiol 1994;160:469-481.

Dingemans KP, Teeling P, Lagendijk JH, Becker AE. Extracellular matrix of the human aortic media: An ultrastructural histochemical and immunohistochemical study of the adult aortic media. Anat Rec 2000;258:1-14.

Gaengel K, Genove G, Armulik A, Betsholtz C. Endothelial-Mural Cell Signaling in Vascular Development and Angiogenesis. Arterioscler Thromb Vasc Biol 2009;29:630-638.

Grainger D, Metcalfe J, Grace A, Mosedale D. Transforming growth factor-beta dynamically regulates vascular smooth muscle differentiation in vivo. J Cell Sci 1998;111:2977-2988.

Hanjaya-Putra D, Bose V, Shen YI, Yee J, Khetan S, Fox-Talbot K et al. Controlled activation of morphogenesis to generate a functional human microvasculature in a synthetic matrix. Blood 2011;118:804-815.

Hellstrom M, Kal n M, Lindahl P, Abramsson A, Betsholtz C. Role of PDGF-B and PDGFR-beta in recruitment of vascular smooth muscle cells and pericytes during embryonic blood vessel formation in the mouse. Development 1999;126:3047-3055.

Hoofnagle MH, Neppl RL, Berzin EL, Teg Pipes GC, Olson EN, Wamhoff BW et al. Myocardin is differentially required for the development of smooth muscle cells and cardiomyocytes. Am J Physiol Heart Circ Physiol 2011;300:H1707-1721.

Izzard TD, Taylor C, Birkett SD, Jackson CL, Newby AC. Mechanisms underlying maintenance of smooth muscle cell quiescence in rat aorta: role of the cyclin dependent kinases and their inhibitors. Cardiovasc Res 2002;53:242-252.

Jin S, Hansson EM, Tikka S, Lanner F, Sahlgren C, Farnebo F et al. Notch signaling regulates platelet-derived growth factor receptor-beta expression in vascular smooth muscle cell. Circ Res 2008;102:1483-1491.

Karnik SK, Brooke BS, Bayes-Genis A, Sorensen L, Wythe JD, Schwartz RS et al. A critical role for elastin signaling in vascular morphogenesis and disease. Development. 2003;130:411-423.

Lee TH, Song SH, Kim KL, Yi JY, Shin GH, Kim JY et al. Functional Recapitulation of Smooth Muscle Cells Via Induced Pluripotent Stem Cells From Human Aortic Smooth Muscle Cells. Circ Res 2010;106:120-128.

Lombardi MAR DM, Schwartz SM. Methodologic considerations important in the accurate quantitation of aortic smooth muscle cell replication in the normal rat. Am J Pathol. 1991;138:441-446.

Mali et al, Butyrate Greatly Enhances Derivation of Human Induced Pluripotent Stem Cells by Promoting Epigenetic Remodeling and the Expression of Pluripotency-Associated Genes. Stem Cells, 28, 713-720 (2010).

Parmacek, MS. Transcriptional programs regulating vascular smooth muscle cell development and differentiation. Curr Top Dev Biol vol. 51: Academic Press:69-89.

Mulvany MJ, Aalkjaer C. Structure and function of small arteries. Physiol Rev 1990;70:921-961.

Nishikawa et al. "Progressive lineage analysis by cell sorting and culture identifies FLK1=VE-cadherin+ cells at a diverging point of endothelial and hemopoietic lineages." *Development*, 125, 1747-1757 (1998).

Nourse, Marilyn B. et al., 'VEGF induces differentiation of functional endotheliun from human embryonic stem cells', Cell Biology/Signaling, Oct. 29, 2009, vol. 30, pp. 80-89.

Owens GK, Kumar MS, Wamhoff BR. Molecular Regulation of Vascular Smooth Muscle Cell Differentiation in Development and Disease. Physiol Rev 2004;84:767-801.

Oyamada N, Itoh H, Sone M, Yamahara K, Miyashita K, Park K et al. Transplantation of vascular cells derived from human embryonic stem cells contributes to vascular regeneration after stroke in mice. J Transl Med. 2008;6:54.

Park S-W, Jun Koh Y, Jeon J, Cho Y-H, Jang M-J, Kang Y et al. Efficient differentiation of human pluripotent stem cells into functional CD34+ progenitor cells by combined modulation of the MEK/ERK and BMP4 signaling pathways. Blood 2010;116:5762-5772.

Patel A, Fine B, Sandig M, Mequanint K. Elastin biosynthesis: The missing link in tissue-engineered blood vessels. Cardiovasc Res 2006;71:40-49.

Phelps EA, Garcia AJ. Update on therapeutic vascularization strategies. Regen Med 2009;4:65-80.

Levenberg S., et al., Blood, 110, 805-814 (2007).

Schenke-Layland K, Rhodes KE, Angelis E, Butylkova Y, Heydarkhan-Hagvall S, Gekas C et al. Reprogrammed Mouse Fibroblasts Differentiate into Cells of the Cardiovascular and Hematopoietic Lineages. Stem cells 2008;26:1537-1546.

Sinha S, Hoofnagle MH, Kingston PA, McCanna ME, Owens GK. Transforming growth factor-beta1 signaling contributes to development of smooth muscle cells from embryonic stem cells. Am J Physiol Cell Physiol. 2004;287:C1560-1568.

Sobue K, Hayashi K, Nishida W, Expressional regulation of smooth muscle cell-specific genes in association with phenotypic modulation. Molecular and Cellular Biochemistry 1999;190:105-18.

Swistowski et al, Efficient Generation of Functional Dopaminergic Neurons from Human Induced Pluripotent Stem Cells Under Defined Conditions. *Stem Cells*, 28, 1893-1904 (2010).

Takahashi K, Tanabe K, Ohnuki M, Narita M, Ichisaka T, Tomoda K et al. Induction of Pluripotent Stem Cells from Adult Human Fibroblasts by Defined Factors. Cell 2007;131:861-872.

Thyberg J. Differences in caveolae dynamics in vascular smooth muscle cells of different phenotypes. Lab Invest 2000;80:915-929.

Tuna BG, Bakker ENTP, VanBavel E. Smooth Muscle Biomechanics and Plasticity: Relevance for Vascular Calibre and Remodelling. Basic Clin Pharmacol Toxicol 2012;110:35-41.

Vazao H, das Neves RP, Graos M, Ferreira L. Towards the maturation and characterization of smooth muscle cells derived from human embryonic stem cells. PLoS One.2011;6:e17771. 5s.

Vodyanik et al, Current protocols in cell biology, Chapter 23 (2007).

Wang D, Chang PS, Wang Z, Sutherland L, Richardson JA, Small E et al. Activation of cardiac gene expression by myocardin, a transcriptional cofactor for serum response factor. Cell 2001;105:851-862.

Wang Z, Wang DZ, Pipes GC, Olson EN. Myocardin is a master regulator of smooth muscle gene expression. Proc Natl Acad Sci U S A 2003;100:7129-7134.

Wolinsky H, Glagov S. A Lamellar Unit of Aortic Medial Structure and Function in Mammals. Circ Res 1967;20:99-111.

Xiao Q, Zeng L, Zhang Z, Hu Y, Xu Q. Stem cell-derived Sca-1+ progenitors differentiate into smooth muscle cells, which is mediated by collagen IV-integrin $\alpha 1/\beta 1/\alpha v$ and PDGF receptor pathways. Am J Physiol Cell Physiol 2007;292:C342-C352.

Xie C, Guo Y, Zhu T, Zhang J, Ma PX, Chen YE. Yap1 Protein Regulates Vascular Smooth Muscle Cell Phenotypic Switch by Interaction with Myocardin. J Biol Chem 2012;287:14598-14605.

Xie W-B, Li Z, Miano JM, Long X, Chen S-Y. Smad3-mediated Myocardin Silencing. J Biol Chem 2011;286:15050-15057.

Xu Y, Stenmark KR, Das M, Walchak SJ, Ruff LJ, Dempsey EC. Pulmonary artery smooth muscle cells from chronically hypoxic neonatal calves retain fetal-like and acquire new growth properties. Am J Physiol Lung Cell Mol Physiol 1997;273:L234-L245.

(56) References Cited

OTHER PUBLICATIONS

Yamamoto M, Yamamoto K, Noumura T. Type I Collagen Promotes Modulation of Cultured Rabbit Arterial Smooth Muscle Cells from a Contractile to a Synthetic Phenotype. Exp Cell Res 1993;204:121-129.
Yamashita J, Itoh H, Hirashima M, Ogawa M, Nishikawa S, Yurugi T et al. Flk1-positive cells derived from embryonic stem cells serve as vascular progenitors. Nature. 2000;408:92-96.
International Search Report for WO2011/106681 mailed Nov. 9, 2011.
International Search Report, PCT/US2013/028341, Jun. 27, 2013.
Abaci et al., (2011). Unforeseen decreases in dissolved oxygen levels affect tube formation kinetics in collagen gels. American Journal of Physiology—Cell Physiology 301, C431-C440.
Abeyta et al., "Unique gene expression signatures of independently-derived human embryonic stem cell lines," Human Molecular Genetics, 2004, vol. 13, pp. 601-608.
Airas et al., (1995). CD73 is involved in lymphocyte binding to the endothelium: characterization of lymphocyte-vascular adhesion protein 2 identifies it as CD73. The Journal of Experimental Medicine 182, 1603-1608.
Allegrucci et al., "Differences between human embryonic stem cell lines," Human Reproduction Update, vol. Advance Access, 2006, pp. 1-18.
Bardin et al., (2001). Identification of CD146 as a component of the endothelial junction involved in the control of cell-cell cohesion. Blood 98, 3677-3684.
Crisan et al., (2008). A Perivascular Origin for Mesenchymal Stem Cells in Multiple Human Organs. Cell Stem Cell 3, 301-313.
Crisan et al., (2012). Perivascular cells for regenerative medicine. Journal of Cellular and Molecular Medicine, 2851-2860.
Dar et al., (2011). Multipotent Vasculogenic Pericytes From Human Pluripotent Stem Cells Promote Recovery of Murine Ischennic Limb / Clinical Perspective. Circulation 125, 87-99.
Dickinson et al., (2010). Guiding endothelial progenitor cell tube formation using patterned fibronectin surfaces. Soft Matter 6, 5109-5119.
Discher et al., (2009). Growth Factors, Matrices, and Forces Combine and Control Stem Cells. Science 324, 1673-1677.
Drukker et al., (2012). Isolation of primitive endoderm, mesoderm, vascular endothelial and trophoblast progenitors from human pluripotent stem cells. Nature Biotechnology 30, 531-542.
Duff et al., (2003). CD105 is important for angiogenesis: Evidence and potential applications. FASEB Journal 17, 984-992.
Extended European Search Report issued in European Patent Application No. 11748168.9 dated Aug. 28, 2013.
Ferreira et al., (2007). Vascular progenitor cells isolated from human embryonic stem cells give rise to endothelial and smooth muscle-like cells and form vascular networks in vivo. Circulation Research 101, 286-294.
Ford et al., "PKH26 and 125I-PKH95: characterization and efficacy as labels for in vitro and in vivo endothelial cell localization and tracking," J. Surg. Res., vol. 62, pp. 23-28. (1996).
Gerecht-Nir et al., "Vascular Development in Early Human Embryos and in Teratomas Derived from Human Embryonic Stem Cells," Biology of Reproduction, 2004, vol. 71, pp. 2029-2036.
Grayson et al., (2010). Engineering anatomically shaped human bone grafts. Proceedings of the National Academy of Sciences of the United States of America 107, 3299-3304.
Haase et al., (2009). Generation of Induced Pluripotent Stem Cells from Human Cord Blood. Cell Stem Cell 5, 434-441.
Hanjaya-Putra et al., (2011). Controlled activation of morphogenesis to generate a functional human microvasculature in a synthetic matrix. Blood 118, 804-815.
Hofmann et al., (2007). Notch Signaling in Blood Vessels: Who Is Talking to Whom About What? Circulation Research 100, 1556-1568.
Huang et al., Differentiation of human embryonic stem cells into smooth muscle cells in adherent monolayer culture. Biochem Biophys Res Commun 2006;351:321-327.
International Search Report issued in PCT Application No. PCT/US2014/030708 dated Jul. 24, 2014.
Kang et al., (2011). Bioengineered human vascular networks transplanted into secondary mice reconnect with the host vasculature and re-establish perfusion. Blood. 6718-6721.
Khetan et al., (2009). Sequential crosslinking to control cellular spreading in 3-dimensional hydrogels. Soft Matter 5, 1601-1606.
Khetan et al., (2010). Patterning network structure to spatially control cellular remodeling and stem cell fate within 3-dimensional hydrogels. Biomaterials 31, 8228-8234.
Kusuma et al., "Self-organized vascular networks from human pluripotent stem cells in a synthetic matrix," PNAS, Jul. 2013, vol. 110, pp. 12601-12606.
Kusuma et al., (2012). The extracellular matrix is a novel attribute of endothelial progenitors and of hypoxic mature endothelial cells. The FASEB Journal. 4925-4936.
Lee et al., (2010). Derivation of neural crest cells from human pluripotent stem cells. Nat Protocols 5, 688-701.
Mali et al., (2010). Butyrate greatly enhances derivation of human induced pluripotent stem cells by promoting epigenetic remodeling and the expression of pluripotency-associated genes. Stem Cells 28, 713-720.
Mead et al., (2007). Isolation and Characterization of Endothelial Progenitor Cells from Human Blood. In Current Protocols in Stem Cell Biology (John Wiley & Sons, Inc.). Supple. 6, Unit 2C.1.
Orlidge et al., (1987). Inhibition of capillary endothelial cell growth by pericytes and smooth muscle cells. The Journal of Cell Biology 105, 1455-1462.
Pittenger et al., (1999). Multilineage potential of adult human mesenchymal stem cells. Science 284, 143-147.
Sainson et al., (2008). Regulation of angiogenesis by homotypic and heterotypic notch signalling in endothelial cells and pericytes: from basic research to potential therapies. Angiogenesis 11, 41-51.
Sato et al., "Molecular signature of human embryonic stem cells and its comparison with the house," Developmental Biology, 2003, vol. 260, pp. 404-413.
Seifert et al., "Vasculogeneic maturation of E14 embryonic stem cells with evidence of early vascular endothelial growth factor independency," Differentiation, 2008, vol. 76, pp. 857-867.
Stewart et al., (2011). Delta-like ligand 4-Notch signaling regulates bone marrow-derived endothelial pericyte/vascular smooth muscle cell formation. Blood 117, 719-726.
Stratman et al., (2009a). Pericyte recruitment during vasculogenic tube assembly stimulates endothelial basement membrane matrix formation. Blood 114, 5091-5101.
Stratman et al., (2009b). Endothelial cell lumen and vascular guidance tunnel formation requires MT1-MMP-dependent proteolysis in 3-dimensional collagen matrices. Blood 114, 237-247.
Thomson, J.A. (1998). Embryonic stem cell lines derived from human blastocysts. Science 282, 1145-1147.
Vodyanik et al., (2010). A mesoderm-derived precursor for mesenchymal stem and endothelial cells. Cell Stem Cell 7, 718-729.
Vunjak-Novakovic et al., (2011). Biomimetic Platforms for Human Stem Cell Research. Cell Stem Cell 8, 252-261.
Wang et al., (2007). Endothelial cells derived from human embryonic stem cells form durable blood vessels in vivo. Nat Biotech 25, 317-318.
Wanjare et al., (2012). Derivation and maturation of synthetic and contractile vascular smooth muscle cells from human pluripotent stem cells. Cardiovascular Research. 321-330.
Woodford et al., "Tissue engineering 2.0: guiding self-organization during pluripotent stem cell differentiation," Current Opinion in Biotechnology, 2012, vol. 23, pp. 810-819.
Yang et al., (2008). Human cardiovascular progenitor cells develop from a KDR+ embryonic-stem-cell-derived population. Nature 453, 524-528.
Zou et al., (2011). Site-specific gene correction of a point mutation in human iPS cells derived from an adult patient with sickle cell disease. Blood 118, 4599-4608.

(56) References Cited

OTHER PUBLICATIONS

Extended European Search Report issued in European Patent Application No. 13754938.2 dated Jul. 17, 2015.

Hashemi et al., "The promotion of stemness and pluripotency following feeder-free culture of embryonic stern cells on collagen-grafted 3-dimensional nanofibrous scaffold," Biomaterials, vol. 32, No. 30, 2011, pp. 7363-7374.

* cited by examiner

SMOOTH MUSCLE-LIKE CELLS (SMLCS) DERVIDED FROM HUMAN PLURIPOTENT STEM CELLS

This application is a National Stage of PCT/US2011/026294 filed Feb. 25, 2011, which claims the benefit of the filing date of U.S. Provisional Patent Application 61/308,014, filed Feb. 25, 2010, both of which are incorporated by reference in their entirety.

BACKGROUND INFORMATION

The vascularization of tissue constructs remains a major challenge in regenerative medicine. Without its own blood supply, an engineered construct relies mainly on diffusional oxygen supply, which can only support a thin layer of viable tissue. Therefore, vascularization of a tissue construct is crucial for its successful implantation, survival, and integration with the host tissue. The formation of mature and functional vascular networks requires interaction between endothelial cells (ECs) and vascular smooth muscle cells (v-SMCs). During early vascular development, ECs line the vessel wall and organize into an immature vasculature. To further stabilize these nascent vessels, ECs secrete platelet-derived-growth-factors (PDGF) to induce the differentiation of specialized mesenchymal stem cells (MSCs) into pericytes in capillaries or SMCs in larger vessels. At this later stage, transforming growth factor-beta 1 (TGF-β1) regulates vessel maturation by inducing v-SMC differentiation and the generation of extracellular matrix (ECM) molecules, such as collagen, fibronectin, and Laminin. Embedded within this ECM, v-SMCs provide physical support to the vasculature and aid in the maintenance of endothelial viability. This process of vascular morphogenesis involving ECs interacting with both the ECM and v-SMCs has been widely studied in vitro using Matrigel assays. When grown on Matrigel, a basement membrane matrix enriched with laminin, ECs and v-SMCs interact to form capillary-like structures (CLSs) that resemble tube formation in vivo. Thus, v-SMCs are key components in engineering vascularized tissue.

One major limitation of this therapeutic approach has been the lack of a reliable source of v-SMCs. Since v-SMCs isolated from patients are usually derived from diseased organs that have limited proliferative capacity and reduced collagen production, they have impaired mechanical strength and cannot support vascular function. Alternatively, bone marrow-derived MSCs have been used to engineer small-diameter vessel grafts and blood vessels which are stable and functional in vivo. Adipose tissue and neural crest tissue also contain populations of multipotent cells that can be differentiated into functional v-SMCs. Another promising source of v-SMCs is human embryonic stem cells (hESCs), which are pluripotent, have high proliferative capacity, exhibit low immunogenicity, and have been shown to repair ischemic tissues and restore blood flow (Sone et al. (2007) *Arterioscler Thromb Vasc Biol* 27, 2127-34). Studies demonstrating the derivation of v-SMCs from embryonic or pluripotent induced stem cells (human or mouse) have utilized various approaches to guide differentiation—such as coculture on OP9 feeder layer or retinoic acid supplementation—and to purify derivatives by sorting for specific vascular progenitors or mature markers, selecting for stable expression of SMC promoter, or isolating the outgrowth of embryoid bodies (EBs). In previous studies, we have demonstrated that the derivation of vascular lineages from hESCs can be achieved by administration of angiogenic growth factors, either by monolayer, two-dimensional (2D) differentiation protocol, or by isolation of vascular progenitor cells or $CD34^+$ cells from 10-day old EBs, followed by selective induction into either endothelial like cells (using vascular endothelial growth factor; VEGF) or smooth-muscle-like cells (SMLCs; using PDGF-BB).

There is a need to develop simple procedure that results in highly purified cultures of SMLCs which are mature enough to exhibit characteristics such as contractile phenotypes and the ability to support vasculature in vitro.

DESCRIPTION OF THE DRAWINGS

FIG. 3A. Expression levels of fibronectin and collagen were examined in hESC-derived SMLCs, and v-SMCs compared to undifferentiated hESCs, using real-time RT-PCR; FIG. 3B. Immunofluorescence staining further demonstrated the expression pattern of fibronectin and collagen in hESC-derived SMLCs and v-SMCs. FIG. 3C. Higher magnification images (of squares in B) demonstrate the intracellular expression (arrowheads) and the secretion (arrows) of fibronectin from hESC-derived SMLC, while fibronectin is expressed intracellular in the v-SMC (arrowheads). Significance levels were set at: # $p>0.05$ and **$p<0.01$. Scale bar is 100 μm.

FIG. 5A. Fluorescent microscopy images of viable CLS formed on Matrigel following seeding with ratios of 100:0, 60:40, 40:60, 20:80, and 0:100 (EPCs:SMLCs). FIG. 5B. Metamorph analysis of CLSs revealed a significant increase of mean tube length (i) and mean tube thickness (ii) and a decrease in complexity (iii) as the ratio of EPC to SMLCs decreased. Significance levels were set at: *$p<0.05$, $p<0.01$, and *$p<0.001$. Scale bar is 20 μm.

FIG. 6A. Representative image showing that CLSs formed from both EPCs and SMLCs. FIG. 6B. Higher magnification Z-stack confocal images (of the squares in A) from top (i), middle (ii), and bottom (iii) show the outer localization of SMLCs and the inner lining EPCs. Scale bar is 100 μm.

DESCRIPTION

Figure 1:
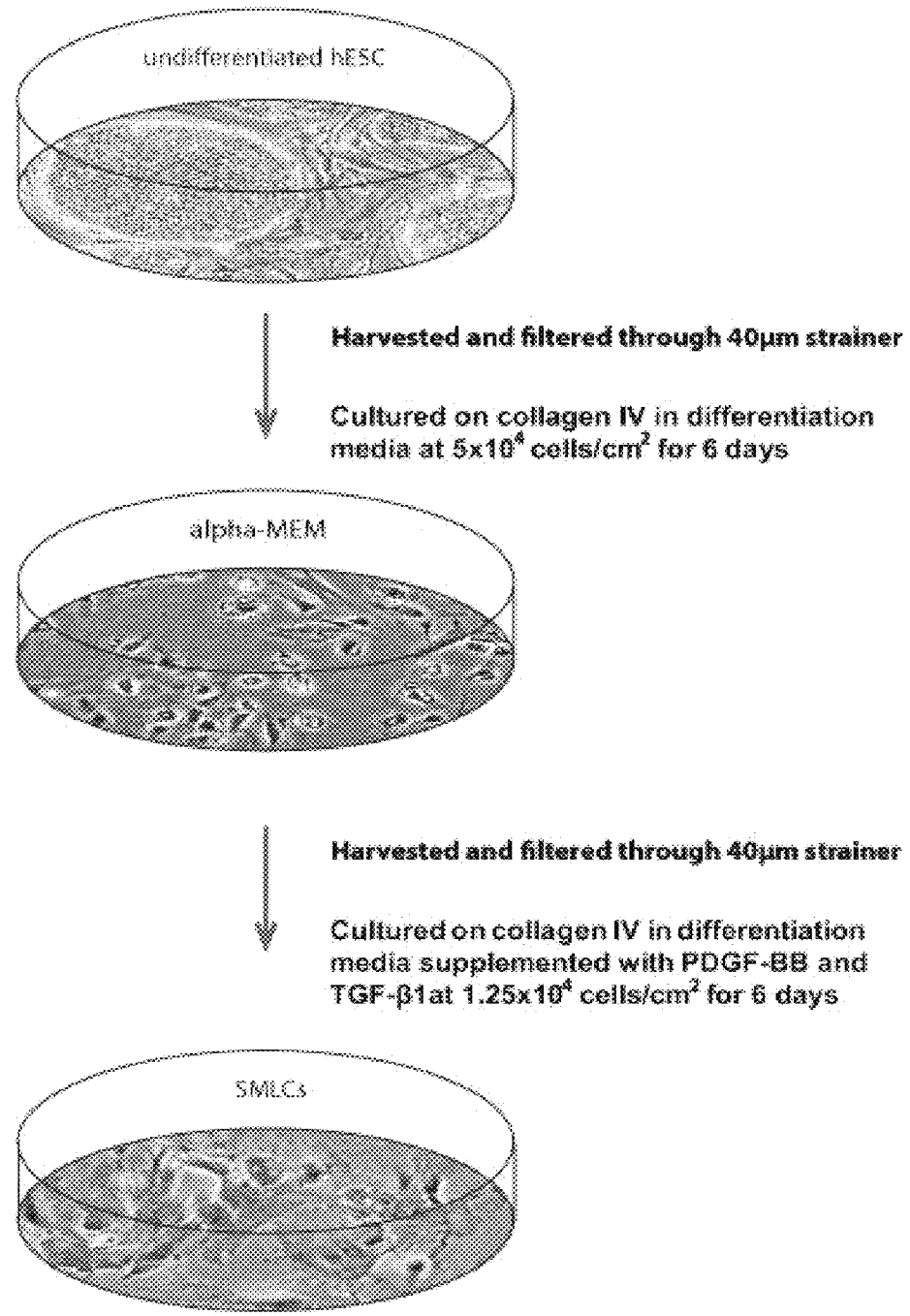
FIG. 1 shows a protocol for the derivation of SMLC from hESCs.

The present inventors describe a step-wise monolayer protocol for differentiating mammalian, including human, pluripotent stem cells (PSCs) into smooth muscle-like cells (SMLCs) in vitro. The PSCs can be derived from any suitable source. For example, they can be embryonic stem cells (ESCs) or induced pluripotent stem cells (abbreviated iPS cells or iPSCs). The method, which is simple, efficient and reliable, allows for the efficient derivation of concentrated, highly purified, relatively mature SMLCs. The derived SMLCs highly express specific smooth muscle (SMC) markers, such as α-smooth muscle actin, calponin, and SM22, and produce and secrete ECM components, such as fibronectin and collagen. Importantly, and unexpectedly, the SMLCs mature to the extent that, e.g., they express relatively high levels of markers of mature SMCs, such as smooth muscle heavy chain (SM-MHC), contract in response to carbachol, and interact with endothelial progenitor cells (EPCs) to support and augment capillary-like vasculature in vitro. The Examples herein present in vitro tubulogenesis assays which show that human ESC-derived SMLCs interact with human endothelial progenitor cells (EPCs) to form longer and thicker cord-like structures in vitro. SMLCs derived by a method of the invention can serve as a ready source for therapeutic vascular tissue engineering.

This invention relates, e.g., to a method for differentiating mammalian pluripotent stem cells (PSCs) into smooth muscle-like cells (SMLCs) in vitro, comprising a) plating a single-cell suspension of PSCs that are smaller than about 50 μm at a seeding concentration of about $5 \times 10^4$ cells/cm$^2$-about $1 \times 10^5$ cells/cm$^2$ onto a suitable surface, and culturing the cells under conditions which prevent the PSCs from aggregating and which induce differentiation of the PSCs into vasculogenic progenitor cells;

b) harvesting the cultured cells of step a) and separating them into a single cell suspension of cells that are smaller than about 50 μm; and c) plating the single cell suspension of step b) at a seeding concentration of about $1 \times 10^4$ cells/cm$^2$-about $5 \times 10^4$ cells/cm$^2$ on a suitable surface, and culturing the cells in a differentiation medium that is supplemented with platelet-derived growth factor BB (PDGF-BB) and transforming growth factor-beta 1 (TGF β1), for a sufficient period of time to allow the vasculogenic progenitor cells to mature into SMLCs.

Optionally, the above method further comprises stretching the cells from step c), by subjecting them to a shear force of at least about 1 dyne/cm$^2$ (e.g., at least 5 dyne/cm$^2$ or at least 10 dyne/cm$^2$) for a time period sufficient to enhance differentiation, maturation and/or functionality of the cells. The shear force may be exerted in a flow chamber such as that shown in FIG. 11.

In any of the embodiments of the invention that are disclosed herein, the PSCs may be human PSCs (hPSCs); the PSCs may be ESCs (e.g., hESCs); the PSCs may be iPSCs (e.g., hiPSCs); and/or the SMLCs may be vascular SMLC (e.g., human vascular SMLCs).

In aspects of the invention, the single cell suspensions are generate by a method that comprises trypsinizing the cells, e.g. with a non-animal alternative for porcine Trypsin that is a recombinant enzyme derived from microbial fermentation sold under the trademark TrypLE™ (Thermo Fisher Scientific), or treating them with EDTA, and/or that comprises sorting the cells through an about 40-μm mesh strainer.

In aspects of the invention, the cells in step a) are plated at a seeding concentration of about $5 \times 10^4$ cells/cm$^2$-about $1 \times 10^5$ cells/cm$^2$, for example at a seeding concentration of about $5 \times 10^4$ cells/cm$^2$-about $7 \times 10^4$ cells/cm$^2$, or about $5 \times 10^4$ cells/cm$^2$. The conditions in step a) that prevent the ESCs from aggregating and induce differentiation of the ESCs into vasculogenic progenitor cells may comprise culturing the cells on an adhesive substrate (e.g., a collagen-type-IV coated culture plate), in a differentiation medium that comprises at least about 5% or at least about 10% serum (v/v), for about 5 to 7 days.

In aspects of the invention, the cells in steps a) and c) are cultured as a monolayer.

In aspects of the invention, the cells in step c) are plated at a seeding concentration of about $1 \times 10^4$-about $5 \times 10^4$ cells/cm$^2$, e.g. at a seeding concentration of less than about $5 \times 10^4$ cells/cm$^2$, less than about $2 \times 10^4$ cells/cm$^2$, or about $1.25 \times 10^4$ cells/cm$^2$. The concentration of PDGF-BB may be about 5 ng/ml-about 50 ng/ml, e.g. about 10 ng/ml. The concentration of TGF-β may be about 1 ng/ml-10 ng/ml., e.g., about 1 ng/ml.

In one aspect of the invention, the cells generated in step c) are subjected to a stress of at least about 1 dyne/cm$^2$ (e.g., at least about 5 dyne/cm$^2$ or at least about 10 dyne/cm$^2$) for at least about 30, 35, 40, 40, 44, 48, 52, 56 or more hours.

One aspect of the invention is a method for differentiating human embryonic stem cells (ESCs) into human smooth muscle-like cells (SMLCs) in vitro, comprising a) plating a single-cell suspension of hESCs that have been filtered through an about 40 μm strainer, to generate a population of cells that are smaller than about 40 μm, at a seeding concentration of about $5 \times 10^4$ cells/cm$^2$, onto a collagen IV coated plate, and culturing the cells in a differentiation medium that comprises about 10% serum, for about 6 days, b) harvesting the cultured cells of step a) and filtering them through an about 40 μm strainer to generate a single cell suspension of cells that are smaller than about 40 μm; and c) plating the single cell suspension of step b) at a seeding concentration of about $1 \times 10^4$ cells/cm$^2$-about $2 \times 10^4$ cells/cm$^2$ on a collagen IV coated plate, and culturing the cells in a differentiation medium comprising about 10% (v/v) of serum and that is supplemented with about 5-50 ng/ml of PDGF-BB and about 1-10 ng/ml of TGF β1, for about 6 days.

Figure 11:
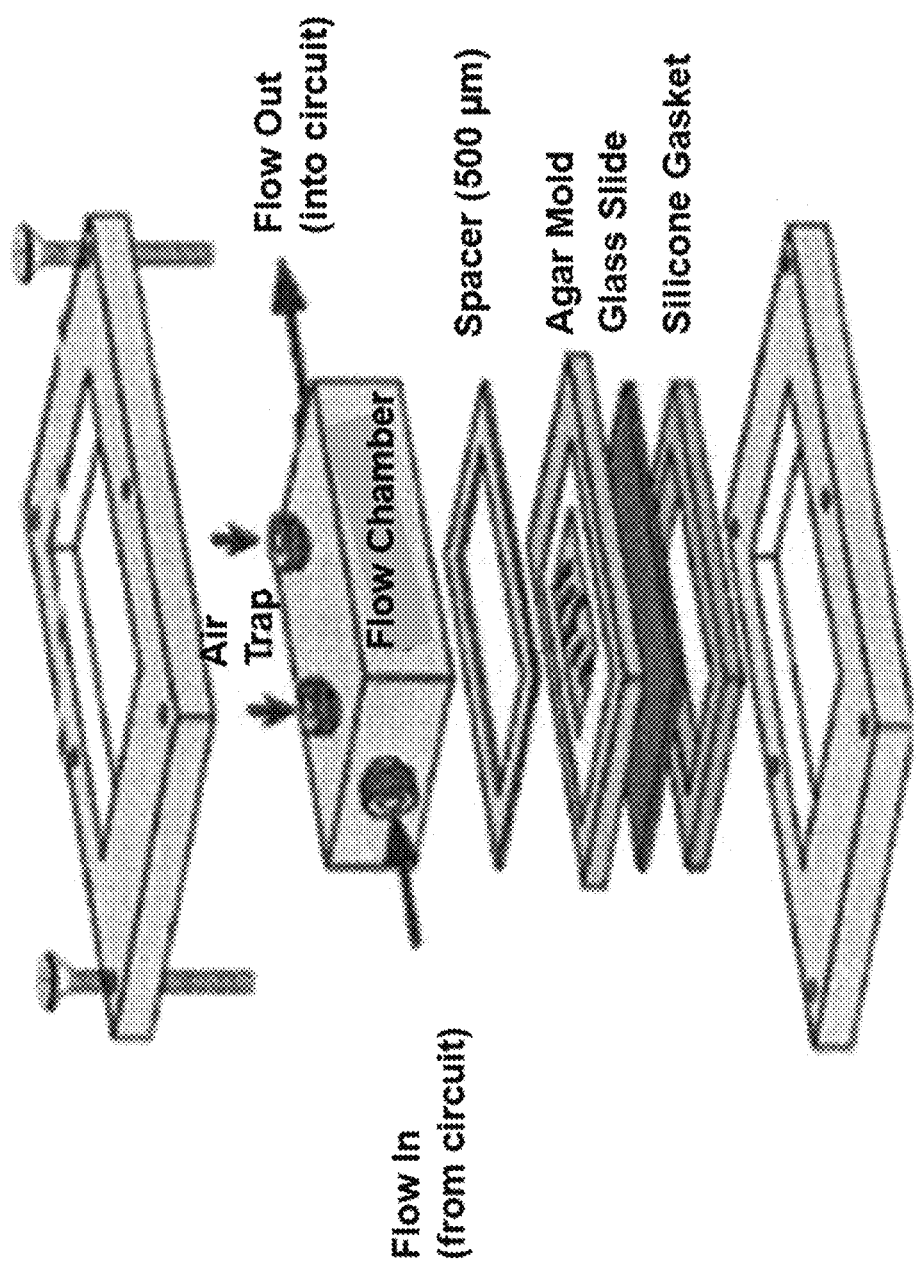
FIG. 11 is a schematic illustration of a flow chamber that can be used for evaluating the effect of shear stress on vasculogenic cells.

Optionally, these steps may be followed by subjecting the cells from step c) to a shear force of at least about 10 dyne/cm$^2$ for at least about 48 hours, in a flow chamber such as that shown in FIG. 11.

Another aspect of the invention is a population (an isolated population) of SMLCs produced by a method of the invention. The cells may have been differentiated from PSCs (e.g., hPSCs), including, for example, ESCs (e.g., hESCs) or iPSCs (e.g., hiPSCs); and/or the SMLCs may be vascular SMLC (e.g., human vascular SMLCs).

These cells may be identical to a population of human smooth muscle cell (SMC), except, for example, that a) in the SMLC population, only about 90-98% of the cells express levels of the SMC markers, α-smooth muscle actin (α-SMA), calponin, and SMC-SM22, at the same level that they are expressed in human aorta v-SMCs; and/or b) only about 50% of the cells express smooth muscle myosin heavy chain (SM-MHC), compared to about 70% of human aorta v-SMCs.

SMLC generated by a method of the invention exhibit properties of matured v-SMCs. For example, they contract in response to carbachol, and they interact with human endothelial progenitor cells (EPCs) to support and augment capillary-like structure (CLS) formation in vitro.

As used herein, the singular forms "a," "an" and "the" include plural referents unless the context clearly dictates otherwise.

Throughout this application, the term "about" is used to mean plus or minus 10% of the value. For example, about $2 \times 10^4$ cells includes $1.8 \times 10^4 - 2.2 \times 10^4$ cells. Ranges as used herein include the endpoints of the range.

"Pluripotent" cells, as used herein, refers to stem that have the potential to differentiate into any of the three germ layers: endoderm (interior stomach lining, gastrointestinal tract, the lungs), mesoderm (muscle, bone, blood, urogenital), or ectoderm (epidermal tissues and nervous system). Pluripotent stem cells can give rise to any fetal or adult cell type. However, alone they cannot develop into a fetal or adult animal because they lack the potential to contribute to extraembryonic tissue, such as the placenta.

Induced pluripotent cells (commonly abbreviated as iPS cells or iPSC) are a type of pluripotent stem cell that is artificially derived from a non-pluripotent cell, such as an adult somatic cell, by forced expression of certain genes. Methods for generating iPS cells are conventional and well-known to those of skill in the art.

Embryonic stem cells (ESCs) are described as "undifferentiated" when a substantial portion of stem cells and their derivatives in the population display morphological characteristics of undifferentiated cells, clearly distinguishing them from differentiated cells of embryonic or adult origin. Undifferentiated ES cells are easily recognized by those skilled in the art, and typically appear in a microscopic view as cells with high nuclear/cytoplasm ratios and prominent nucleoli. Similarly, undifferentiated cells can be distinguished from differentiated cells by the absence of lineage specific markers such as vascular endothelial growth factor receptor 2 (VEGFR2), vascular endothelial cadherin (VE-cad) or platelet-endothelial cell adhesion molecule-1 (PECAM-1).

Often, hESCs are cultured with mouse embryonic fibroblasts (MEFs), a layer of feeder cells that nurture the hESCs and keep them in undifferentiated state. In some embodiments of the invention, endothelial progenitor cells (EPCs) are sometimes expended on a feeder layer.

Much of the discussion in the present application is directed to ESCs. However, other forms of PSCs, such as iPSCs, are included.

In a method of the invention, in the first culture step, individual undifferentiated ES cells are cultured in a manner suitable for inducing differentiation into vasculogenic progenitor cells.

Before being plated and cultured, the ESCs, which often have been grown on a feeder layer, are treated with a suitable reagent (e.g., digested with trypsin, such as TrypLE, or treated with EDTA) to detach them from the culture plate, and are treated further to generate a single-cell suspension of cells that are smaller than about 50 μm (e.g., about 40 μm or smaller). The sizing step not only sorts the cells into cells of a desired size, but also separates them from undesirable, larger cells, such as feeder layer cells (e.g., MEFs) or EPC that may be present in the culture. Sizing methods such as filtration can also help to break up cells that have adhered to one another, e.g., in ESC colonies. Without wishing to be bound by any particular mechanism, it is suggested that filtering ESCs also minimizes cell-cell contact, thereby increasing vascular differentiation efficiency. Furthermore, it is suggested that smaller cells are more proliferative than larger ones, and are more likely to continuously differentiate.

The sizing step can be accomplished by a variety of methods. For example, various filtration, morphometry and/or densitometry approaches can be used.

Methods of filtration are well known in the art, such as the passage through a mesh, sieve, filter and the like. Filters can comprise a fibrous matrix or porous material. Such filters may be one of several commercially available filters including but not limited to cell culture filters from Pall Life Sciences (Ann-Arbor Mich., USA) or BD-Falcon (Boston, Mass., USA). One suitable type of filter is a nylon mesh filter having a pore size of 40 μm (Cell Cultureware, BD-Falcon, Boston, Mass.).

"Morphometry" refers to the measurement of external form, and can employ methods including but not limited to 2-D and 3-D image analysis. Advanced imaging analysis software suitable for identification and isolation of cells smaller than 50 μm is commercially available to one skilled in the art [see, for example, Metamorph Software (Universal Imaging Corp., Downing Pa., USA), Imagic-5 (Image Science Software, Berlin, Germany) and Stereologer (Systems Planning and Analysis, Inc., Alexandria, Va., USA)] and can be combined with well known light microscopy and flow sorting techniques for selection of objects of desired external characteristics (e.g. size) (for suitable apparatus see, for example, U.S. Pat. No. 6,249,341 to Basiji et al).

"Densitometry" refers to measurement of the optical or physical density of an object. Densitometric measurements may be used to characterize and provide criteria for separation and isolation of cells. Devices suitable for densitometric isolation of endothelial-like cells are, for example, the MECOS-C1 blood cell densitometry analyzer (MECOS Co., Moscow, Russia). Cells may also be separated by sedimentation through a preparative density gradient such as FICOLL™ or PERCOLL™ (Amersham Biosciences, Inc. Piscataway, N.J. USA) (for exhaustive review of densitometric fractionation techniques, see Pertoft, H J Biochem Biophys Methods 2000; 44:1-30). Thus, the present invention provides an easy and rapid approach to progenitor cell generation and isolation. Previous methods of isolating such progenitor cells have produced progenitor populations which lack desirable proliferation capabilities, limiting their practical application (Reubinoff, B E et al Nat Biotech 2000; 18:399-404, and Schuldiner, M et al PNAS USA 2000; 97:11307-312). The vasculogenic progenitor cells isolated by the methods of the present invention are capable of generating large numbers of identical cells by proliferation through numerous cell doublings.

The undifferentiated ES cells utilized in the method of the present invention can be mammalian embryonic stem cells obtained from any suitable source, including fresh or cryo-preserved embryonic cell masses, cells from in-vitro-fertilized embryonic cell masses and/or cultured ES cell lines. In the protocol illustrated in FIG. 1, the undifferentiated ESC are cultured cell lines, which have been propagated on suitable feeder layers. The ES cells may be from any mammalian source from which ES cells can be obtained. These include, e.g., certain laboratory animals such as mice, farm animals, sporting animals, and domestic animals or pets. Non-human primates and humans are included. Much of the present application is directed to the use of human ESCs, but it is to be understood that other sources of ESCs are included.

As used herein, the phrase "vasculogenic progenitor cells" refers to a population of cells that can generate progeny that are endothelial or smooth muscle precursors (such as angioblasts) or mature endothelial or smooth muscle cells, or hematopoietic precursor (such as erythroid colony forming units and megakaryocytes) or mature blood cells (such as erythrocytes and leukocytes). Typically, vasculogenic progenitor cells express some of the phenotypic markers that are characteristic of the endothelial, smooth muscle and hematopoietic lineages. Typically, they do not produce progeny of other embryonic germ layers when cultured by themselves in vitro, unless dedifferentiated or reprogrammed. It will be appreciated that it is not implied that each of the cells within the population have the capacity of forming more than one type of progeny, although individual cells that are multipotent vasculogenic progenitor cells may be present.

As is shown, for example, in the Examples herein, differentiation of individual undifferentiated ES cells can be effected by culturing such cells on plates coated with an adhesive substrate such as type IV collagen, laminin or gelatin to prevent aggregation of the ES cells; seeding the cells at a low plating density (at a seeding concentration of about $5 \times 10^4$ cells/cm$^2$-about $1 \times 10^5$ cells/cm$^2$, for example about $5 \times 10^4$ cells/cm$^2$-about $7 \times 10^4$ cells/cm$^2$, or about $5 \times 10^4$ cells/cm$^2$); and providing differentiation medium that contains no growth factors. In one embodiment, individual undifferentiated ES cells are grown on type IV collagen-coated plates (available from, for example, Cell Cultureware, BD-Falcon, Boston, Mass.). See the Examples section for further description of conditions for differentiation of ES cells.

As used herein, the term "differentiation medium" refers to a suitable medium capable of supporting growth and differentiation of the ES cells. Examples of suitable differentiation media which can be used with the present invention include a variety of growth media prepared with a base of alpha MEM medium (Life Technologies Inc., Rockville, Md., USA) or Dulbecco's minimal essential medium (DMEM) supplemented with 10% FBS (HyClone, Logan, Utah, USA) and 0.1 mM β-mercaptoethanol (Life Technologies Inc., Rockville, Md., USA). The cells generated in this first culture step are a mixed population of cells, including vasculogenic progenitor cells. Following a suitable amount of time to generate a desirable number of vascular progenitor cells (e.g., about 5-7 days), the cells are harvested, trypsinized and sorted to generate a single-cell suspension of cells that are smaller than 50 μm in size, by methods such as those described above.

In a second round of differentiation, a single cell suspension of cells from the first round of culture is once again plated onto plates coated with an adhesive substrate such as type IV collagen, at a low seeding density. The adhesive substrate helps prevent aggregation of the cells. The inventors have found that a low plating density, of about $1 \times 10^4$-about $5 \times 10^4$ cells/cm$^2$, (e.g., less than about $2.5 \times 10^4$ cells/cm$^2$; less than about $2.0 \times 10^4$ cells/cm$^2$; about $1 \times 10^4$-about $2 \times 10^4$ cells/cm$^2$; or about $1.25 \times 10^4$ cells/cm$^2$)-results in effective differentiation of the vasculogenic progenitor cells to SMLCs. Much of the discussion in this application is directed to the differentiation into vascular smooth muscle or vascular smooth muscle-like cells. However, it is to be understood that a method of the invention can be used to differentiate ESCs into any type of smooth muscle or smooth muscle-like cell.

In this second differentiation step, the cells are again cultured in a differentiation medium, but this time the medium is supplemented with platelet-derived growth factor BB (PDGF-BB) and transforming growth factor-beta 1 (TGF β1). In addition, in order to guide the differentiation of the vasculogenic progenitor cells into vascular smooth muscle-like cells rather than into endothelial cells (EC), it is beneficial to use a high concentration of serum in the medium. In embodiments of the invention, the serum concentration is higher than about 5%, higher than about 9%, or higher than about 10% (v/v).

Under the culture conditions in this second round of cell culture, the cells differentiate into SMLCs. A skilled worker can readily determine the optimal time for this differentiation to occur. For example, the cells can be incubated for 5-7 (e.g. 6) days.

Optionally, the SMLCs obtained from the second round of culture can be treated further by applying shear stress and "stretching" them, a process which enhances differentiation, maturation and/or functionality of the cells. In this procedure, the cells are exposed to a shear force of at least about 1 dyne/cm$^2$ (e.g., at least about 5 dyne/cm$^2$ or at least about 10 dyne/cm$^2$) for a time period sufficient to enhance differentiation, maturation and/or functionality of the cells. In one embodiment of the invention, the exposure of the SMLCs to a shear force is effected by using a flow chamber such as illustrated in FIG. 11. SMLCs are cultured in a flow chamber and are exposed to flow-induced shear stress for about 24 hours or about 48 hours. A closed-loop flow circuit circulates sterile SMC-differentiation medium through the assembled flow chamber, which inflicts a steady, laminar shear stress of 10 dynes/cm$^2$ acting upon the cells. Each experiment is accompanied by a static control construct. Following about a 24 hr exposure to shear stress the cells are removed from culture and analyzed.

Figure 10:
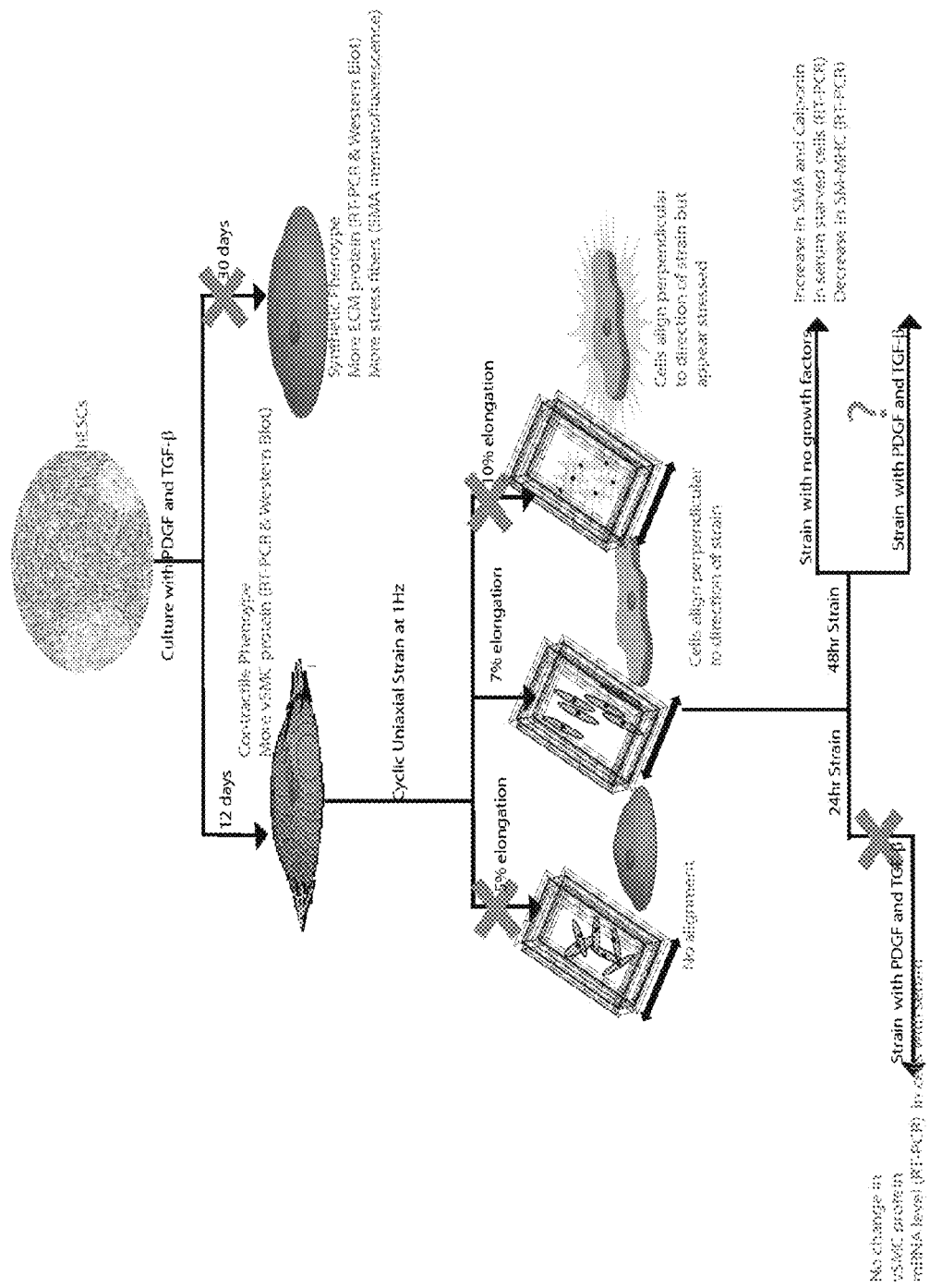
FIG. 10 is a cartoon showing that the application of stress to SMLCs can, under certain conditions, enhance the maturation of the cells toward being SMCs.

As is shown in the cartoon in FIG. 10, a treatment with cyclic uniaxial strain at 1 Hz and 7% elongation of the cells under appropriate conditions leads to the cells aligning perpendicularly to the direction of strain; the cells exhibit a healthy phenotype and appearance. A lower or higher % elongation leads to either no alignment, or to alignment of the cells perpendicular to the direction of strain, but the cells appear stressed. That is, the cell morphology is distorted; cell spread is substantially decreased; and the cells appear to be on the verge of detaching. Under the 7% elongation conditions, the optimal conditions appear to be about 48 hours of strain, with no growth factors or serum present in the differentiation medium. Under these conditions, there is an increase in SMA (a specific marker indicative of early vascular smooth muscle cells) and calponin, as determined by RT-PCR, and a decrease in SM-MHC, also as determined by RT-PCR. It is expected that 48 hours of strain in the presence of PDGF and TGF-β will lead to similar results. These studies indicate that cyclic strain effectively induces expression and organization kinetics of stress fibers, thereby enhancing differentiation, maturation and functionality of ES-derived vasculogenic cells.

Populations of smooth muscle-like cells produced by a method of the invention are smooth muscle-"like" because, although they are similar to, they are not identical to, naturally occurring populations of mature smooth muscle cells. For example, the Examples herein show that in a population of v-SMLC cells generated by a method of the invention, only about 90-98% of the cells express levels of certain SMC markers, such as α-smooth muscle actin (α-SMA), calponin, and SMC-SM22, at the level that they are expressed in human aorta v-SMCs. Furthermore, smooth muscle myosin heavy chain (SM-MHC), which is a marker for mature SMCs, is expressed in about 70% of human aorta v-SMCs, but it is only expressed in abut 50% of v-SMLCs. It is expected that with further minor refinements of a method of the invention, including the introduction of the "stretching" step, cells differentiated by a method of the invention will eventually be much more similar to SMCs.

Nevertheless, the inventors show herein that v-SMLCs produced by a method of the invention are unexpectedly considerably more highly purified, at a higher concentration, and at a more advanced level of maturity than cells differentiated in vitro by other methods. In particular, the v-SM-LCs exhibit a number of functional properties that are characteristic of SMCs, such as those shown in FIGS. 3-6 herein. For example, v-SMLCs exhibit the ability to contract in response to pharmacological drugs such as carbachol, and they support avascular network (When allowed to interact with human endothelial progenitor cells (EPCs), they support and augment CLS formation).

SMCLs and methods of the invention have a variety of uses, which are discussed in U.S. Pat. No. 7,354,763, which is incorporated by reference herein, particularly with regard to those disclosures.

In the foregoing and in the following examples, all temperatures are set forth in uncorrected degrees Celsius; and, unless otherwise indicated, all parts and percentages are by weight.

EXAMPLES

Example I

Materials and Methods

Cell Culture

All cells were cultured in humidified incubators (37° C.) in atmospheres maintained with 5 percent $CO_2$.

Human ESCs.

Human ESC line H9 was grown (passages 15 to 40; WiCell Research Institute, Madison, Wis.) on an inactivated mouse embryonic fibroblast feeder layer (Globalstem, Rockville, Md.) in growth medium consisting of 80 percent ES-DMEM/F12 (Globalstem) supplemented with 20 percent knockout serum replacement (Invitrogen, Carlsbad, Calif.) and 4 ng/ml basic fibroblast growth factor (bFGF; Invitrogen), as previously described (Gerecht-Nir et al. (2003) *Laboratory Investigation* 83, 1811-20). Human ESCs were passaged every four to six days with 1 mg/ml of type IV collagenase (Invitrogen). Media were changed daily.

Human v-SMCs.

Human aorta v-SMCs (ATCC, Manassas, Va.) served as the control cell type and were grown in the specified ATCC complete SMC growth medium, consisting of Kaighn's Modification of Ham's F-12 Medium (F-12K Medium; ATCC), 10 percent fetal bovine serum (FBS; Hyclone), 0.05 mg/ml ascorbic acid (Sigma-Aldrich, St. Louis, Mo.), 0.01 mg/ml insulin (Sigma), 0.01 mg/ml Transferrin (Sigma), 10 ng/ml sodium selenite (Sigma), 0.03 mg/ml Endothelial Cell Growth Supplement (Sigma), HEPES (Sigma) to a final concentration of 10 mM, and TES (Sigma) to a final concentration of 10 mM. Human v-SMCs were passaged every three to four days with 0.25 percent trypsin (Invitrogen). Media were changed every two to three days.

Human EPCs.

Human umbilical cord EPCs isolated from outgrowth clones, kindly provided by Dr. Yoder, Indiana University School of Medicine, were expanded and used for experiments between passages 3 and 10. For the current study, EPCs were isolated from seven healthy newborns (three females and four males; gestational age range, 38-40 weeks), pooled, expanded, and characterized according to a previously established protocol by Yoder and colleagues, and as we describe in details in our recent publication (Hanjaya-Putra et al. (2009) *J Cell Mol Med*). Briefly, EPCs were expanded in flasks coated with type I collagen (Roche Diagnostics, Basel, Switzerland), in endothelial growth medium (EGM; PromoCell Heidelberg, Germany) supplemented with 1 ng/ml $VEGF_{165}$ (Pierce, Rockford, Ill.), and incubated in a humidified incubator at 37° C. in an atmosphere containing 5% $CO_2$. EPCs were passaged every three to four days with 0.05% trypsin (Invitrogen, Carlsbad, Calif.) and characterized for the positive expression of cell-surface antigens CD31, CD141, CD105, CD144, vWF and Flk-1, and the negative expression of hematopoietic-cell surface antigens CD45 and CD14. Single cell colony forming assays were used to characterize their robust proliferative potential, secondary and tertiary colony formation upon replating.

V-SMC Differentiation Protocol

Human ESCs were digested with TrypLE (Invitrogen). Cells were separated into an individual cell suspension using a 40-μm mesh strainer. The individual hESCs were plated onto collagen-type-IV-coated plates (R&D Systems, Minneapolis, Minn.) in a concentration of $5 \times 10^4$ cells/$cm^2$. These cells were cultured in a differentiation medium of alpha-MEM (Invitrogen) with 10 percent FBS and 0.1 mM β-mercaptoethanol (Invitrogen) for six days. Media were changed every day. On day six, differentiated cells were removed using trypLE, filtered through a 40 μm mesh strainer (BD Biosciences, San Jose, Calif.), and recultured onto collagen-type-IV-coated plates in cell concentrations of $1.25 \times 10^4$ cells/$cm^2$ in differentiation medium supplemented with PDGF-BB (10 ng/ml) and TGF-β1 (1 ng/ml) for six days (both from R&D Systems). Media were changed every second day.

Real-Time Quantitative RT-PCR

Two-step RT-PCR was performed on hESCs, v-SMCs, and differentiated SMLCs after six days in the growth-factor-supplemented differentiation medium. Total RNA was extracted by using TRIzol (Gibco, Invitrogen), according to the manufacturer's instructions. Total RNA was quantified by an ultraviolet spectrophotometer, and the samples were validated for having no DNA contamination. RNA (1 μg per sample) was subjected to reverse transcriptase using M-MLV (Promega Co., Madison, Wis.) and oligo(dT) primers (Promega), using the manufacturer's instructions. We used TaqMan Universal PCR Master Mix and Gene Expression Assay (Applied Biosystems, Foster City, Calif.) for COL, FN1, KDR, PDGFRB, NEUROPILIN, SMA, ANG-1, FLT-1, VE-CAD, β-ACTIN, and HPRT1, according to the manufacturer's instructions. The TaqMan PCR step was performed with an Applied Biosystems StepOne Real-Time PCR System (Applied Biosystems), following the manufacturer's instructions. The relative expression of COL1A1 or FN1 was normalized to the amount of HPRT1 or β-ACTIN in the same cDNA by using the standard curve method described by the manufacturer.

For each primer set, the comparative computerized tomography method (Applied Biosystems) was used to calculate amplification differences between the different samples. The values for experiments were averaged and graphed with standard deviations.

Immunofluorescence

After six days in growth-factor-supplemented differentiation medium, hESC-derived SMLCs were fixed using 3.7% formaldehyde fixative for 15 minutes and washed with Phosphate buffered saline (PBS). After, cells were permeabilized with a solution of 0.1% Triton-X (Sigma) for ten minutes, washed with PBS, and incubated for one hour with anti-human SMA (1:200; Dako, Glostrup, Denmark), anti-human calponin (1:200; Dako), anti-human SM22 (1:200, Abeam, Cambridge, Mass.), and anti-human SM-MHC (1:100; Dako). For ECM staining, cells were incubated with anti-human fibronectin (1:200; Sigma) or anti-human collagen (1:200; Abeam) for one hour. Cells were rinsed twice with PBS and incubated with anti-mouse IgG Cy3 conjugate (1:50; Sigma) or anti-rabbit IgG Alexa Fluor 488 conjugate (1:1000; Molecular Probes, Eugene, Oreg.) for one hour, rinsed with PBS, and incubated with DAPI (1:1000; Roche Diagnostics) for ten minutes. Coverslips were rinsed once more with PBS and mounted with fluorescent mounting medium (Dako). The immunolabeled cells were examined using fluorescence microscopy (Olympus BX60; Olympus, Center Valley, Pa.).

Fluorescence-Activated Cell Sorting (FACS)/Flow Cytometry

After six and twelve days of differentiation, hESC-derived SMLCs cells were treated with 0.25% trypsin for five minutes, counted, and separated into approximately $2 \times 10^5$ cells per vial. They were then incubated in either FITC- or PE-conjugated antigen specific antibodies for VEGFR-2/KDR, PDGFR-B, α-SMA (R&D systems) for one hour on ice. For detection of intracellular markers, cells were fixed with 3.7% formaldehyde for ten minutes and permeabilized with 0.1% Triton-X for ten minutes prior to incubation with antibodies. For other SMC markers, mouse anti-human SMA (1:200), mouse anti-human calponin (1:200), mouse anti-human SM-MHC (1:10; Dako), and rabbit anti-human SM22 (1:2000; Abeam) were used. Cells were rinsed with 0.1% bovine serum albumin (BSA), and then incubated in the anti-mouse IgG FITC conjugate (1:50; Molecular Probes) or anti-rabbit IgG Alexa Fluor 488 conjugate (1:1000; Molecular Probes) for one hour. Afterwards, cells were strained and suspended in 0.1% BSA. All analysis was done using isotype controls corresponded to each specific antibody. User guide instructions were followed to complete the FACS analysis.

Tube Formation Assay on Matrigel

Matrigel (BD Bioscience) was cast into each well of a μ-Slide Angiogenesis (iBidi, Munich, Germany) and allowed to polymerize inside the incubator for one hour. For each well, 100,000 cells/cm² of EPCs and hESC-derived SMLCs were seeded with respective ratios of 100:0, 60:40, 40:60, 20:80, and 0:100 in EGM (PromoCell) supplemented with 1 ng/ml $VEGF_{165}$ (Pierce). Visualization and image acquisition were performed using an inverted light microscope (Olympus IX50) at time intervals of 12, 24, and 48 hours.

Quantification of CLSs

After 12 hours of culture on Matrigel, the LIVE/DEAD Viability/Cytotoxicity Kit (Invitrogen) was used to visualize CLSs, following the manufacturer's protocol. Briefly, calcein AM dye was diluted in phenol-red-free DMEM (Invitrogen) to obtain a final concentration of 2 μM. The constructs were incubated with the dye solution for 30 minutes. After replacing with fresh phenol-red-free DMEM, CLSs were visualized using a fluorescent microscope with a 10× objective lens (Axiovert; Carl Zeiss Inc., Thornwood, N.Y.). As previously described[30], we analyzed four image fields per construct from three distinct experiments (n=3) performed in triplicate, using Metamorph software 6.1 (Universal Imaging Co., Downingtown, Pa.) to quantify and compare CLSs formed on each substrate.

Spatial Organization of EPCs and SMLCs in CLSs

To analyze the position of EPCs and hESC-derived SMLCs within the forming CLSs, both cell types were labeled: EPCs with PKH2 (green) and SMLCs with PKH-26 (red) (Sigma), according to the manufacturer's protocol. Briefly, EPCs and differentiated SMLCs suspensions in diluent C were mixed with PKH2 and PKH-26, respectively, for five minutes. The staining was stopped by adding Heat Inactivated-FBS (Globalstem), and the cells were washed three times with EGM medium (PromoCell) supplemented with 1 ng/ml $VEGF_{165}$ (Pierce) and 2% HI-FBS (Globalstem). The cells were seeded for tube formation assays on Matrigel (BD Bioscience) in EGM media and cultured for 12 hours. A sequence of z-stack images was obtained using confocal microscopy (LSM 510 Meta; Carl Zeiss) to determine the spatial arrangement of the cells in the CLSs.

Functional Contraction Studies

Contraction studies in response to pharmacological drugs were done, as previously described.[12, 22] Briefly, hESC derived-SMLCs cultured for three passages were washed, and contraction was induced by incubating with $10^{-5}$ M carbachol (Calbiochem, Darmstadt, Germany) in DMEM medium (Invitrogen) for 30 minutes. In a separate experiment, the cells were induced to relax by incubating with muscarinic antagonist $10^{-4}$ M atropine (Sigma) in DMEM for one hour and then induced to contract with $10^{-5}$ M carbachol. The cells were visualized using cytoplasm-viable fluorescence dye, as described in the "Quantification of CLSs" section, above. A series of time-lapse images were taken using a microscope with a 10× objective lens (Axiovert; Carl Zeiss). The cell contraction percentage was calculated by the difference in area covered by the cells before (at time zero) and after contraction (at time 30 minutes).

Statistical Analysis

We performed statistical analyses of CLS quantification, fibronectin and collagen production, and contractility data using GraphPad Prism 4.02 (GraphPad Software Inc., La Jolla, Calif.). Unpaired Student's t-tests were performed, and significance levels were set at *p<0.05, p<0.01, and *p<0.001, respectively. No significant difference (p>0.05) was indicated with #. All graphical data were reported.

Example II

Results

Derivation of SMLCs from hESCs

Our protocol, which is shown in FIG. 1, efficiently derives SMLCs from hESCs. At the first stage, to reduce the pluripotency associated with autocrine signaling, we utilized TrypLE to ensure a single-cell suspension and decreased cell seeding concentrations to $2.5 \times 10^4$ cells/cm². In addition to supplementation of culture media with 10 ng/ml PDGF-BB, we added 1 ng/ml TGF-β1.

Characterization of hESC-Derived SMLCs

Figure 2:
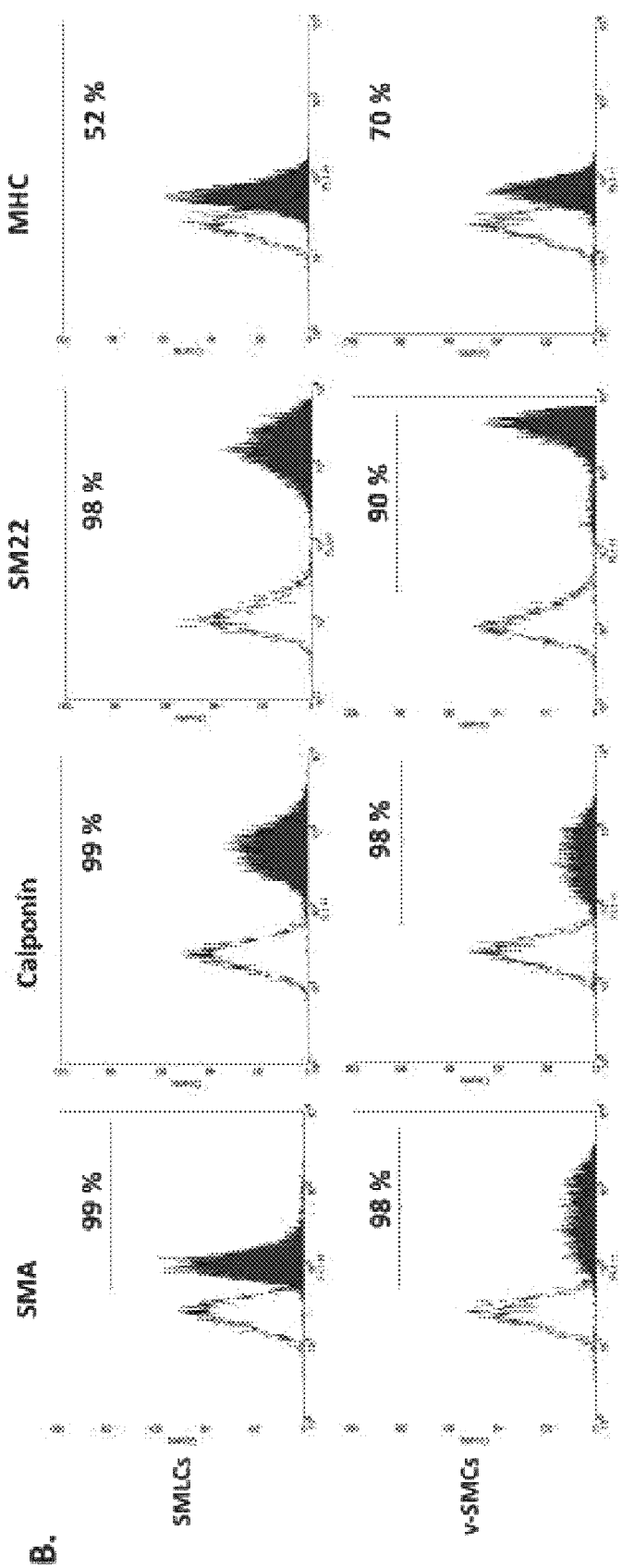
FIG. 2 shows the characterization of hES C-derived SMLCs. Human ESC-derived SMLCs were analyzed for the expression of specific SMCs markers, including SMA, calponin, SM22 and SM-MHC, using flow cytometry.
Figure 3:
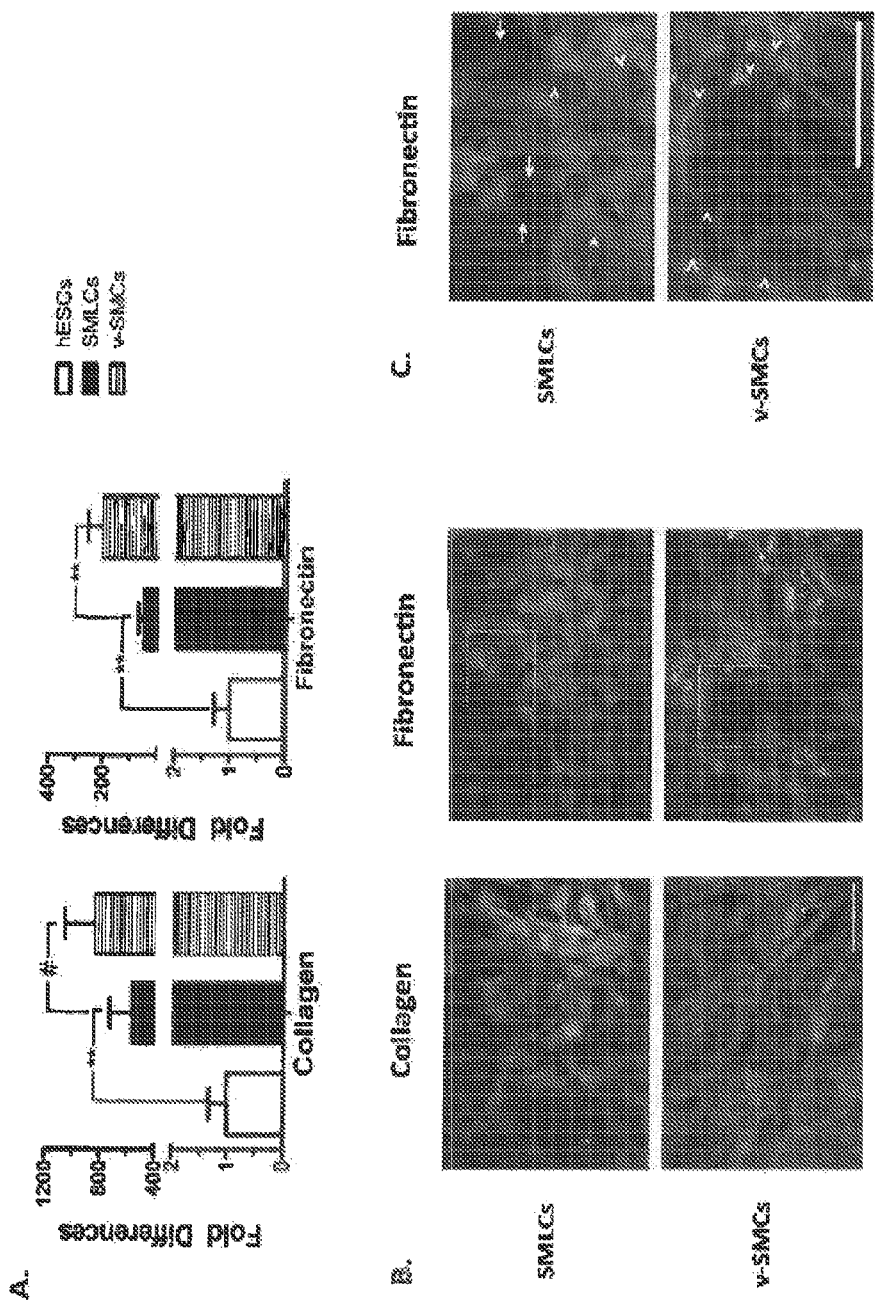
FIG. 3 shows ECM production and secretion.
Figure 7:
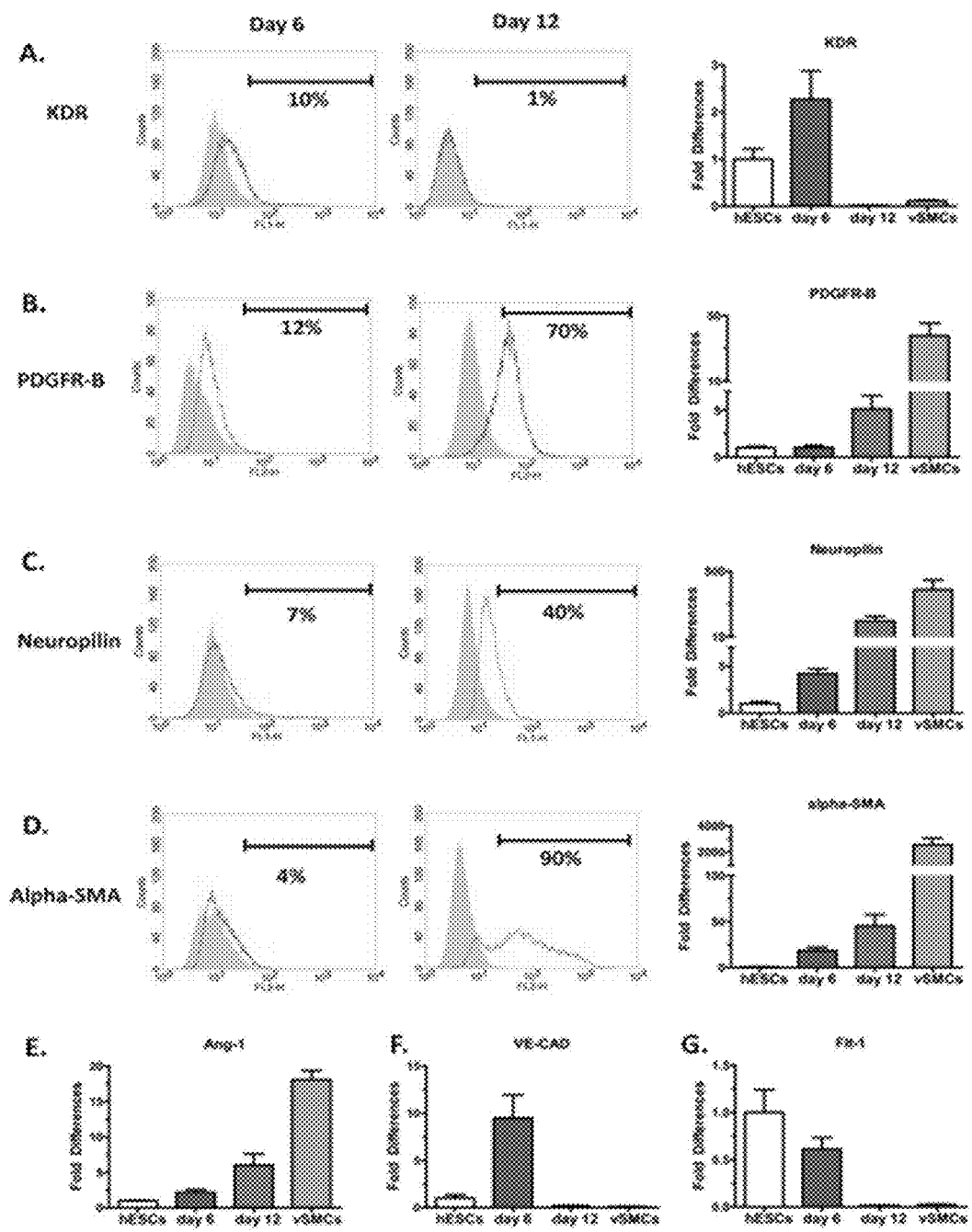
FIG. 7 shows marker expression kinetics. Differentiating hESCs were analyzed on day 6 and 12 using FACS and real-time PCR for: A. KDR; B. PDGFRB; C. Neuropilin; D. SMA; E. Ang-1; F. VE Cad; G. Flt-1.

After 12 days of differentiation, hESC-derived SMLCs were analyzed for specific v-SMC markers and compared to human aorta v-SMCs. The chosen markers are proven indicators of v-SMC lineage, including α-SMA, an actin isoform typical of SMCs and present in high amounts in v-SMCs (Gong et al. (2008) *FASEB Journal* 22, 1635-48); calponin, a calcium-binding protein that normally functions to inhibit ATPase activity in v-SMCs (Sobue et al. (1999) *Molecular and Cellular Biochemistry* 264, 18272-5); SM22 alpha, an actin cross-linking/gelling protein that belongs to the calponin family (Duband et al. (1993) *Differentiation* 55, 1-11); and SM-MHC, a contractile protein specific for the SMC lineage (Kuro-o et al. (1989) *Journal of Biological Chemistry* 264, 18272-5; Aikawa et al. (1993) Circ Res 107, 2085-8). Human ESC-derived SMLCs, like human aorta v-SMCs, were found to express SMA, calponin, SM22, and SM-MHC within the cell cytoplasm (data not shown). Flow cytometry analysis (using indirect labeling) further showed high expression levels of most markers in hESC-derived SMLCs, which were comparable to their expression levels in human aorta v-SMCs—including SMA (99 vs. 98 percent, respectively), calponin (99 vs. 98 percent, respectively), and SM22 (98 vs. 90 percent, respectively)—while SM-MHC was expressed in hESC-derived SMLCs to a lesser extent than its expression in human aorta v-SMCs (52 vs. 70 percent, respectively) (FIG. 2). To better understand the kinetics of gene regulation, we further analyzed differentiating cells at day 6 and day 12 for markers known to be involved in mesodermal/vascular differentiation. It was previously demonstrated that KDR is expressed in undifferentiated hESCs and continues to be expressed during differentiation associated with embryoid body formation. We found that using our differentiation protocol, KDR is down-regulated, as demonstrated by both FACS and qRT-PCR analyses (FIG. 7A). Other markers related to SMC specification are upregulated throughout the differentiation including: PDGFR-B, Neuropilin, and SMA, as well as Angiopoietin 1 (Ang-1) production (FIG. 7B-E). We also show that VE-Cad and FLT-1, which are known to be involved in endothelial cell commitment, are downregulated along the SMC lineage commitment (FIG. 7F-G).

ECM Production by hESC-Derived SMLCs

Figure 8:
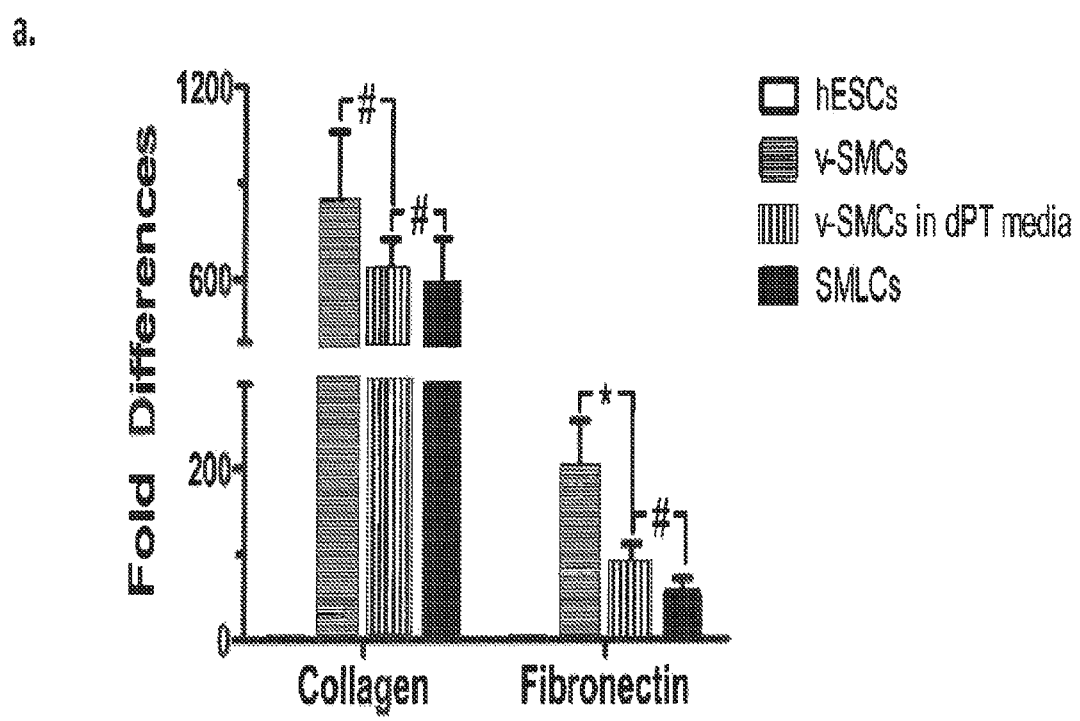
FIG. 8 shows fibronectin and collagen production. Human ESCs, human aorta v-SMCs, human aorta v-SMCs grown in differentiation media, and hESC-derived SMLCs were analyzed for their collagen and fibronectin expression. Significance levels were set at: # $p>0.05$ and *$p<0.05$. Scale bar is 100 p.m.
Figure 9:
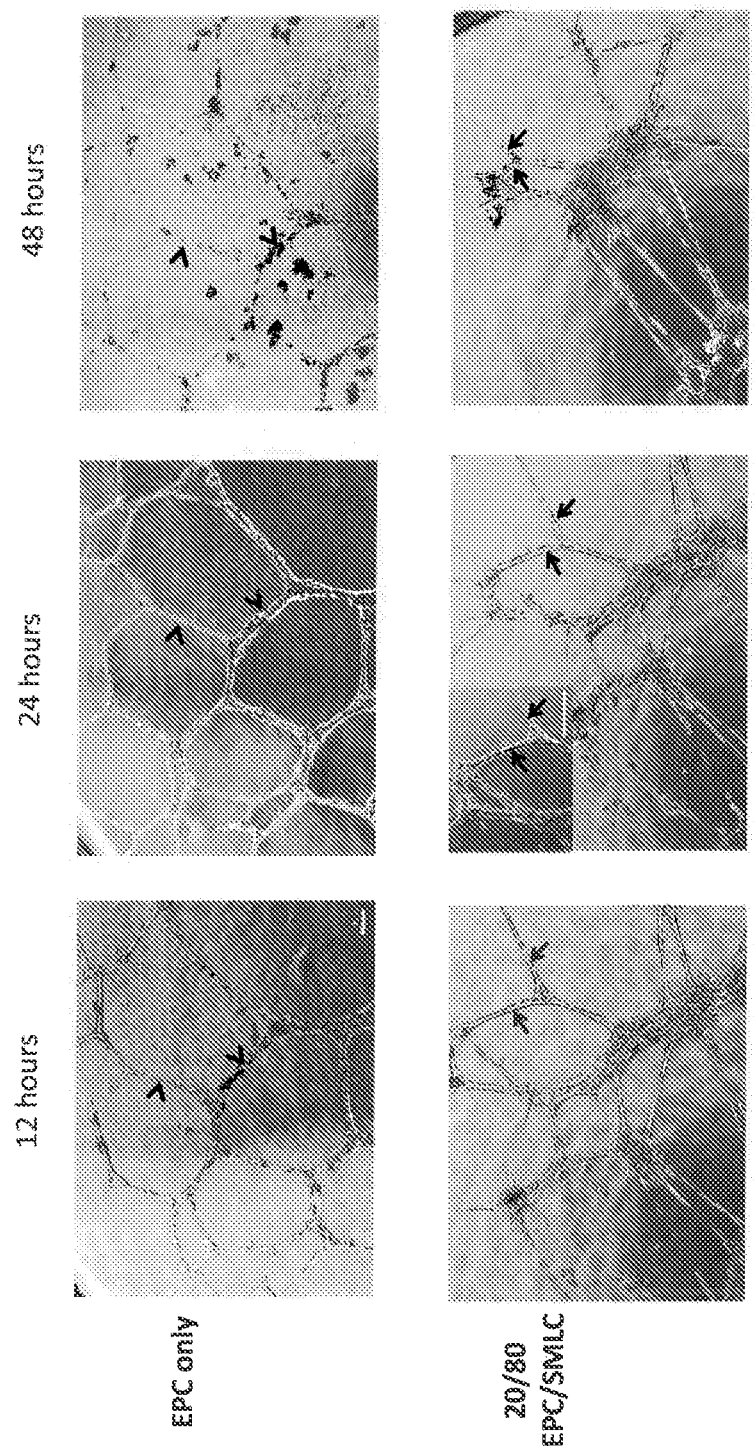
FIG. 9 shows time-lapse images of CLSs formation on Matrigel. Within 12 hours, both EPCs only and 20:80 EPCs:SMLCs formed in vitro CLSs on Matrigel. CLSs formed by EPC only became thinner over time (indicated by arrowheads) and underwent apoptosis, collapsing into their nodes after 48 hours of culture. However, CLSs formed with both EPC and SMLC (20:80) were found to form thicker tubes and stabilized after 48 hours (indicated by arrows).

To explore the potential of hESC-derived SMLCs to support engineered vasculatures, we examined the production of the ECM molecules fibronectin and collagen. Realtime PCR analysis revealed that, compared to undifferentiated hESCs, hESC-derived SMLCs produced 565-fold more collagen and 52-fold more fibronectin (FIG. 3A). We found no significant difference in collagen production between hESC-derived SMLCs and human aorta v-SMCs, while slightly lower, but significant, expression levels of fibronectin were observed in hESC-derived SMLCs compared to human aorta v-SMCs (FIG. 3A). It should be noted that culturing human aorta v-SMCs in differentiation media of hESC-derived SMLCs resulted in decreased expression of fibronectin, suggesting an inhibitory effect of differentiation media compared to v-SMC media (FIG. 8). Immunofluorescence analysis revealed that hESC-derived SMLCs lay down their own ECM, including fibronectin and collagen (FIG. 3B). However, unlike human aorta v-SMCs, where fibrous fibronectin was observed mainly within the cells' cytoplasm, fibronectin produced by hESC-derived SMLCs was found both within the cells and outside on the Petri dish (FIG. 3C), indicating ECM secretion by hESC-derived SMLCs. No significant differences in the ECM secretion pattern were observed when human aorta v-SMCs were cultured in differentiation media (data not shown). Overall, this data provides insight into the early developmental stage of hESC-derived SMLCs and their potential to support developing vasculatures.

Contraction of hESC-Derived SMLCs

Figure 4:
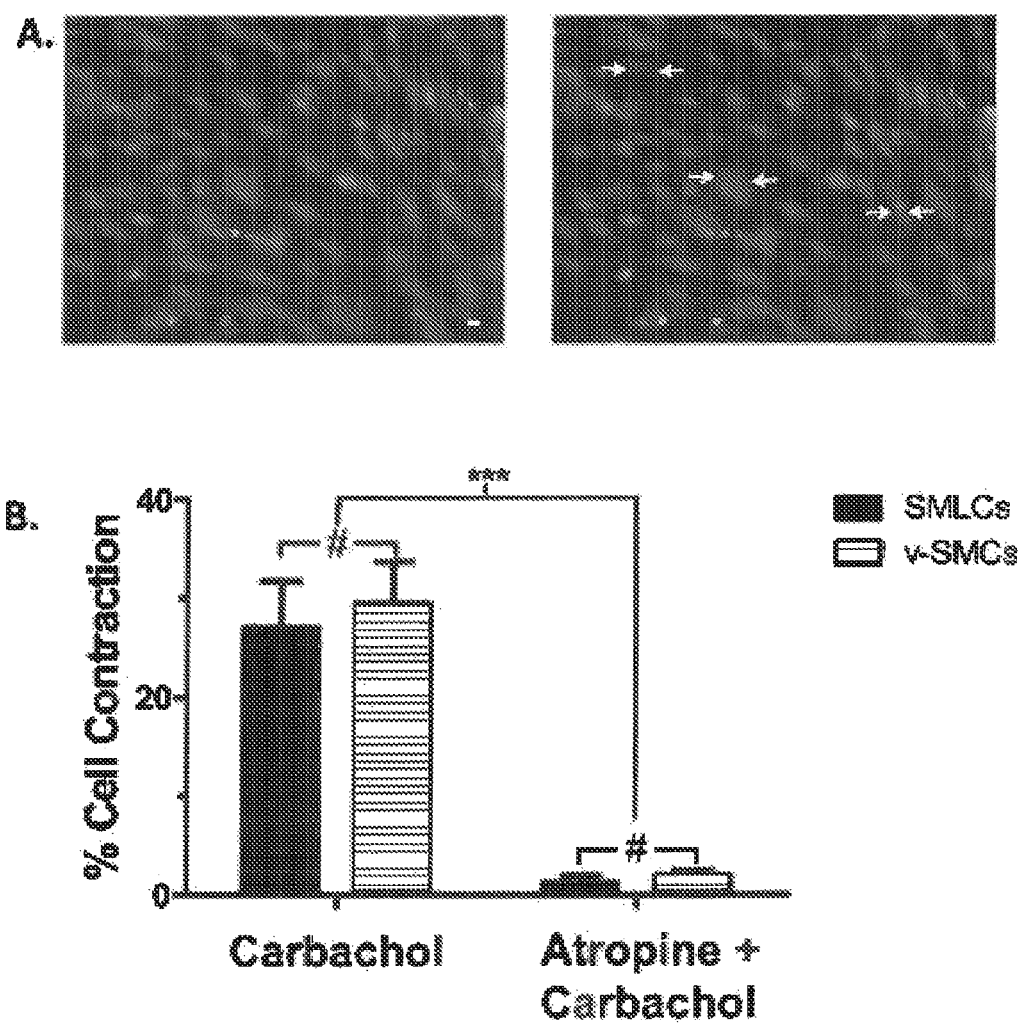
FIG. 4 shows contractility of hESC-derived SMLCs. Quantitative contractility of hESC-derived SMLCs and human aorta v-SMCs. Significance levels were set at: # $p>0.05$ and **$p<0.01$.

The primary function of v-SMCs is to contract and relax within the blood vessel wall to maintain its integrity. To examine whether hESC-derived SMLCs can contract, the cells were subjected to carbachol, which induces contraction in v-SMCs, and atropine, which blocks contractility. Human ESC-derived SMLCs were found to contract in response to carbachol ($10^{-5}$ M), as demonstrated by a series of time-lapse images. Morphological changes of hESC-derived SMLCs were clearly observed following treatment with carbachol, with cytoplasm-viable fluorescence dye showing shrinkage of contracting cells after treatment (data not shown), Contraction was quantified by the difference in cell area between time zero and time 30 minutes. Contractions of hESC-derived SMLCs were not significantly different than those of human v-SMCs (FIG. 4). Furthermore, the muscarinic antagonist atropine ($10^{-4}$ M) was shown to significantly block the carbachol-mediated contractility (FIG. 4).

Human ESC-Derived SMLCs Augmented Capillary-Like Structure (CLS) Phenotype

Cord-blood-derived hEPCs have been shown to form functional and stable blood vessels. We previously used EPCs to study in vitro capillary tube formation induced by substrate nanotopography and viscoelasticity (Bettinger et al. (2008) *Adv Mater* 20, 99-103). Therefore, to study the ability of hESC-derived SMLCs to support an engineered vascular network, we examined in vitro formation of CLSs from cocultures of human EPCs and SMLCs. We seeded human EPCs and hESC-derived SMLCs at ratios of 100:0, 60:40, 40:60, 20:80, and 0:100 (EPCs:SMLCs) on Matrigel. After 12 hours, CLS formation was observed in all conditions (FIG. 5A), while SMLCs supported longer and thicker tubes, with less complex networks (FIG. 5B). Moreover, SMLCs were found to stabilize and prolong CLS formation on Matrigel, which otherwise collapsed after 48 hours (FIG. 8). It should be noted that CLSs formed by both EPCs and SMLCs were found to break down by clumping at around 60 to 72 hours after seeding (data not shown).

Human ESC-Derived SMLCs Coherently Positioned with EPCs During CLS Formation

Figure 5:
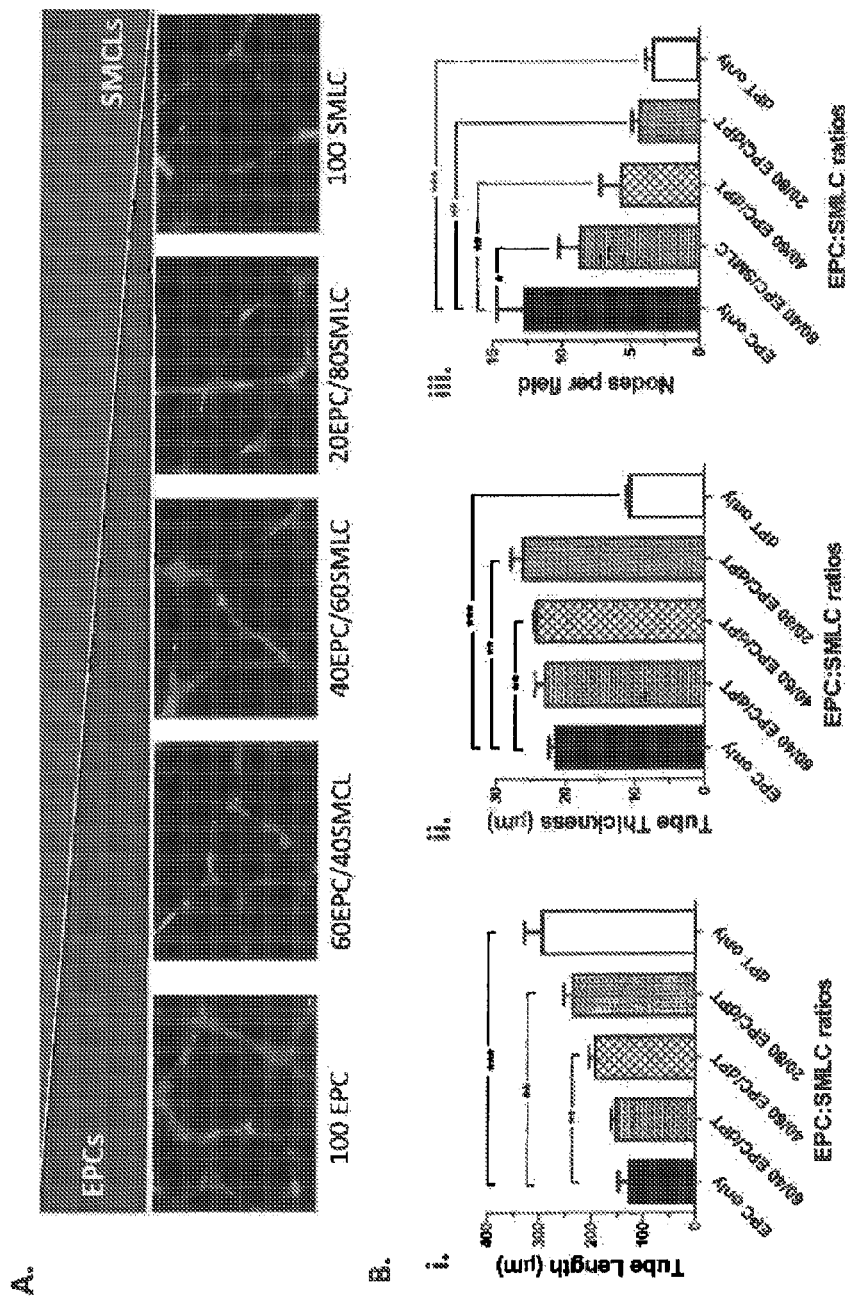
FIG. 5 shows that human ESC-derived SMLCs support in vitro vascular network formation and stabilization.
Figure 6:
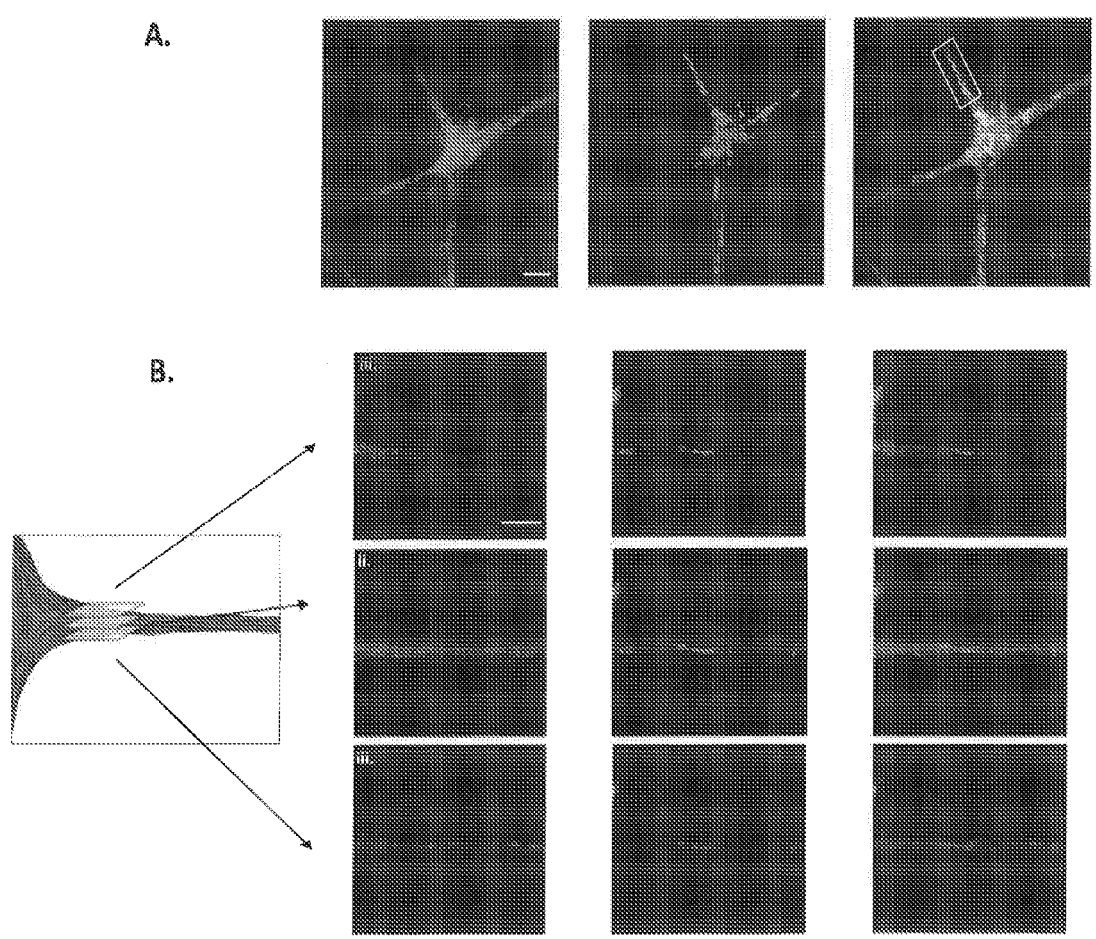
FIG. 6. Organization of SMLCs and EPC in CLS. EPCs and hESC-derived SMLCs were dyed in green and red (respectively) and seeded at ratio of 20:80 (EPCs:SMLCs) on Matrigel.

To examine whether SMLCs participate in CLS formation, a series of confocal z-stack analyses was performed on CLSs formed by EPCs and SMLCs (20:80) which showed the longest and thickest tubes (FIG. 5). We found that all CLSs contained both SMLCs and EPCs (FIG. 6A), where, in most cases, SMLCs were found to wrap the inner lining EPCs, providing a supportive layer for the developing network (FIG. 6B).

Discussion

One of the major issues in therapeutic vascularization is finding a reliable source from which cells can be isolated with high efficiency, purity, and minimal manipulation. In addition to the emerging sources of SMCs from MSCs, adipose tissues, and neural crests, hESCs offer a unique source of cells for understanding signaling during vascular development and for therapeutics to treat the vasculature. Our previous study demonstrated that vascular progenitors derived from hESCs could be induced to differentiate into both ECs and SMLCs by exposure to VEGF or PDGF-BB, respectively (Ferreira et al. (2007) *Circ Res* 101, 286-94). This differentiation protocol required sorting of the vascular progenitors from developing EBs, followed by their seeding as a monolayer to induce lineage commitment. In the present application, we built on that protocol to differentiate hESCs into vascular lineages using a monolayer differentiation protocol. We utilized this method to better control the differentiation processes and tuning of the supplemented growth factors. We have shown here that when hESCs are seeded as single cells in a certain cell density on collagen-IV-coated plates, efficient guidance of their differentiation is achieved. Without wishing to be bound by any particular mechanism, it is suggested that this may be due to reduced autocrine signaling. These adherent cells grew for six days in differentiation media without growth factor supplementation to promote lateral mesoderm cell differentiation (Gerecht-Nir et al. (2003) (supra)). After six days, the cells were harvested, sorted through a 40-μm strainer, and recultured on collagen-IV-coated plates in differentiation media containing 10 ng/ml PDGF-BB and 1 ng/ml TGF-β1 for an additional six days to induce lineage commitment to v-SMCs. By the end of 12 days, FACS and immunofluorescence analysis revealed highly purified, differentiated SMLCs, more than 90% of which expressed levels of α-SMA, calponin, and SMC-SM22 that were comparable to levels in human aorta v-SMCs. However, only 52% of these SMLCs expressed SM-MHC, a mature marker of SMCs, compared to 70% expression by human aorta v-SMCs. Our data also indicate that KDR+ cells give rise to these SMLCs, as its expression is downregulated throughout the differentiation period.

Real-time RT-PCR showed that these hESC-derived SMLCs highly expressed collagen and fibronectin, which are crucial for SMCs to support vascular development. SMLCs produced collagen in levels comparable to human aorta v-SMC while producing fibronectin to a lesser extent than human aorta v-SMCs. This could be attributed to the differentiation media, which also yielded reduced expression of fibronectin in human aorta v-SMCs cultured in this differentiation media. Interestingly, immunofluorescence analysis revealed that, in hESC-derived SMLCs, fibrous fibronectin was located both within the cells and outside the cells on the Petri dish, indicating that hESC-derived SMLCs secrete fibronectin to the extracellular space. This favorable result suggests that hESC-derived SMLCs can be used for therapeutic vascularization, as SMCs tend to show a decrease in ECM production as they age. Furthermore, hESC-derived SMLCs were found to contract in response to carbachol, while atropine blocks this contraction, a response similar to that observed in human aorta v-SMCs.

Mature vascular SMCs are highly specialized cells which can perform both synthetic function, to support blood vessels, and contractile function, to regulate blood pressure. During early vascular morphogenesis, SMCs and mural cells are recruited to stabilize the nascent capillary through cytokine interactions and ECM production. In later stages, in response to their local environment (i.e., shear stress), these SMCs acquire a contractile phenotype. Hence, engineering functional vascular networks requires both phenotypes, synthetic at the early stage of vascular morphogenesis and contractile at the later stage of vascular stabilization. Here, we report the derivation of SMLCs from hESCs with emerging synthetic SMC phenotype and contractility responsiveness. Together, these results indicate that hESC-derived SMLCs, although in an early stage of development, are functional and may be able to support in vitro engineered vasculature.

To study the ability of hESC-derived SMLCs to support engineered vascular networks, we examined in vitro formation of CLSs from cocultures of human EPCs and SMLCs. As the ratio of EPC to SMLCs decreased, we found that SMLCs supported longer and thicker tubes, with less complex networks. Moreover, SMLCs were able to stabilize and prolong CLS formation on Matrigel, which would otherwise collapse after 48 hours of culture. These results support previous observations suggesting that pericytes might stabilize CLSs by altering the EC phenotype to reflect a more differentiated state. Without wishing to be bound by any particular mechanism, it is suggested that SMLCs may stabilize CLSs in vitro by both cytokine interactions and physical arrangement, by wrapping the inner lining of EPCs, providing a supportive layer for the developing network. These in vitro results also agree with previous in vivo studies where cocultured, differentiated MSCs were shown to stabilize vessel formation of EPCs.

Collectively, these results indicate that the improved derivation protocol of the invention will lead to highly purified cultures of hESC-derived SMLCs. Such SMLCs have early stage v-SMC characteristics, and hESC-derived SMLCs have the potential to support engineered vascular networks in vitro and therefore should be considered as a potential cell source for therapeutic vascularization.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications (including provisional patent application Provisional Patent Application 61/308,014, filed Feb. 25, 2010) cited above and in the figures are hereby incorporated in their entirety by reference, particularly with regard to the method or finding for which they are cited.

We claim:

1. A method for differentiating human pluripotent stem cells (hPSCs) into human smooth muscle like cells (SMLCs) in vitro, comprising
   a) plating a single-cell suspension of hPSCs that are smaller than 50 μm at a seeding concentration of about $5 \times 10^4$ cells/cm$^2$-about $1 \times 10^5$ cells/cm$^2$ onto a suitable surface, and culturing the cells under conditions which prevent the hPSCs from aggregating and which induce differentiation of the hPSCs into vasculogenic progenitor cells;
   b) harvesting the cultured cells of step a) and separating them into a single cell suspension of cells that are smaller than 50 μm;
   c) plating the single cell suspension of step b) at a seeding concentration of about $1 \times 10^4$ cells/cm$^2$-about $5 \times 10^4$ cells/cm$^2$ on a suitable surface, and culturing the cells in a differentiation medium that is supplemented with platelet-derived growth factor BB (PDGF-BB) and transforming growth factor-beta 1 (TGF β1); and
   d) stretching the cells from step c) by subjecting the cells to a flow-induced shear stress for a time period sufficient to enhance differentiation, maturation and/or functionality of the cells
   wherein the human SMLCs are characterized by at least one of up regulated PDGFR-B, up regulated Calponin, up regulated SMA, up regulated Ang-1, and/or reduced expression of fibronectin, as compared to human aorta vascular smooth muscle cells.

2. The method of claim 1, wherein the flow-induced shear stress applied to the cells from step c), is at least 1 dyne/cm$^2$.

3. The method of claim 1, wherein the flow-induced shear stress is exerted in a flow chamber.

4. The method of claim 1, wherein the hPSCs are human embryonic stem cells (hESCs).

5. The method of claim 1, wherein the hPSCs are induced pluripotent stem cells (iPSCs).

6. The method of claim 5, wherein the iPSCs are human iPSCs.

7. The method of claim 1, wherein the SMLCs are human vascular SMLCs.

8. The method of claim 1, wherein the method to generate single cell suspensions comprises trypsinizing the cells with TrypLE.

9. The method of claim 1, wherein the single cell suspensions of cells that are smaller than 50 μm are generated by a method comprising sorting the cells through a 40-μm mesh strainer.

10. The method of claim 1, wherein the cells in step a) are plated at a seeding concentration of about $5 \times 10^4$.

11. The method of claim 1, wherein the conditions in step a) that prevent the hPSCs from aggregating and induce differentiation of the hPSCs into vasculogenic progenitor cells comprise culturing the cells on an adhesive substrate, in a differentiation medium that comprises at least about 5% serum (v/v), for about 5 to 7 days.

12. The method of claim 11, wherein the adhesive substrate is collagen-type-IV coated culture plate.

13. The method of claim 11, wherein the differentiation medium comprises at least about 10% serum (v/v).

14. The method of claim 1, wherein the cells in steps a) and c) are cultured as a monolayer.

15. The method of claim 1, wherein the cells in step c) are plated at a seeding concentration of less than about $2 \times 10^4$ cells/cm$^2$.

16. The method of claim 1, wherein the cells in step c) are plated at a seeding concentration of about $1.25 \times 10^4$ cells/cm$^2$.

17. The method of claim 1, wherein in step c), the concentration of PDGF-BB is about 5 ng/ml-about 50 ng/ml.

18. The method of claim 17, wherein in step c), the concentration of PDGF-BB is about 5 ng/ml-about 10 ng/ml.

19. The method of claim 1, wherein in step c), the concentration of TGF-β is about 1 ng/ml-about 10 ng/ml.

20. The method of claim 19, wherein the concentration of TGF-β is about 1 ng/ml.

21. The method of claim 1, wherein the cells generated in step c) are subjected to a stress of at least 1 dyne/cm$^2$ for at least about 48 hours.

22. The method of claim 21, wherein the stress is at least 5 dyne/cm$^2$.

23. The method of claim 21, wherein the stress is at least 10 dyne/cm$^2$.

24. A method for differentiating human embryonic stem cells (hESCs) into human smooth muscle-like cells (SMLCs) in vitro, comprising
  a) plating a single-cell suspension of hESCs that have been filtered through a 40 μm strainer, to generate a population of cells that are smaller than 40 μm, at a seeding concentration of about $5 \times 10^4$ cells/cm$^2$, onto a collagen IV coated plate, and culturing the cells in a differentiation medium that comprises about 10% serum, for about 6 days,
  b) harvesting the cultured cells of step a) and filtering them through a 40 μm strainer to generate a single cell suspension of cells that are smaller than 40 μm;
  c) plating the single cell suspension of step b) at a seeding concentration of less than about $2 \times 10^4$ cells/cm' on a collagen IV coated plate, and culturing the cells in a differentiation medium comprising about 10% (v/v) of serum and that is supplemented with about 10 ng/ml of PDGF-BB and about 1 ng/ml of TGF β1, for about 6 days; and
  d) stretching the cells from step c) by subjecting the cells to a flow-induced shear stress for at least 48 hours;
  wherein the flow-induced shear stress is exerted in a flow chamber, and
  wherein the human SMLCs are characterized by at least one of up regulated PDGFR-B, up regulated Calponin, up regulated SMA, up regulated Ang-1, and/or reduced expression of fibronectin, as compared to human aorta vascular smooth muscle cells.

25. The method of claim 24, wherein the flow-induced shear stress is at least 10 dyne/cm$^2$.

* * * * *